(12) United States Patent
Piron et al.

(10) Patent No.: US 9,241,765 B2
(45) Date of Patent: Jan. 26, 2016

(54) OPEN ARCHITECTURE IMAGING APPARATUS AND COIL SYSTEM FOR MAGNETIC RESONANCE IMAGING

(71) Applicant: HOLOGIC, INC., Marlborough, MA (US)

(72) Inventors: Cameron Anthony Piron, Toronto (CA); Christopher Luginbuhl, Toronto (CA); Donald B. Plewes, Toronto (CA)

(73) Assignee: Invivo Corporation, Andover, MA (US)

( * ) Notice: Subject to any disclaimer, the term of this patent is extended or adjusted under 35 U.S.C. 154(b) by 0 days.

(21) Appl. No.: 14/034,459

(22) Filed: Sep. 23, 2013

(65) Prior Publication Data

US 2014/0024926 A1    Jan. 23, 2014

Related U.S. Application Data

(63) Continuation of application No. 12/139,123, filed on Jun. 13, 2008, now Pat. No. 8,571,632, which is a continuation of application No. 11/442,944, filed on Aug. 28, 2006, now Pat. No. 7,970,452, which is a (Continued)

(51) Int. Cl.
*A61B 5/055* (2006.01)
*A61B 19/00* (2006.01)
(Continued)

(52) U.S. Cl.
CPC .............. *A61B 19/20* (2013.01); *A61B 5/0555* (2013.01); *A61B 8/0825* (2013.01); *A61B 8/0841* (2013.01); *A61B 8/406* (2013.01);
(Continued)

(58) Field of Classification Search
CPC .. A61B 10/0233; A61B 19/20; A61B 19/201; A61B 19/203; A61B 2017/3411; A61B 2017/3413; A61B 2019/205; A61B 2019/5236; A61B 2019/5276; A61B 2019/5408; A61B 5/0555; A61B 8/0825; A61B 8/0841; A61B 8/406; A61B 8/4416; A61B 8/5238; G01S 7/52049
USPC ................ 600/411, 422; 324/318, 322; 5/601
See application file for complete search history.

(56) References Cited

U.S. PATENT DOCUMENTS

| | | |
|---|---|---|
| 3,115,140 A | 12/1963 | Volkman |
| 4,503,844 A | 3/1985 | Siczek |

(Continued)

FOREIGN PATENT DOCUMENTS

| | | |
|---|---|---|
| CN | 1640139 A | 7/2005 |
| CN | 101601266 A | 12/2009 |

(Continued)

OTHER PUBLICATIONS

European Search Report mailed Mar. 1, 2012 for European Patent Application No. 07800538.6, 8 pages.

(Continued)

*Primary Examiner* — Michael Rozanski

(57) ABSTRACT

Apparatus and method for using radio frequency coil systems for magnetic resonance imaging within an open architecture apparatus is provided. The MRI coil system includes a support structure with an open architecture in which secondary support structures, compression systems and plates containing RF coil systems may be introduced. These structures and RF coils can be moved relative to the patient, or removed entirely from the system. In one embodiment the system consists of a tabletop coil system, while another embodiment consists of a dedicated stretcher design.

20 Claims, 14 Drawing Sheets

Related U.S. Application Data continuation-in-part of application No. 10/916,738, filed on Aug. 12, 2004, now Pat. No. 7,379,769, application No. 14/034,459, which is a continuation of application No. 13/112,208, filed on May 20, 2011, now Pat. No. 8,560,051, which is a continuation of application No. 11/442,944, filed on Aug. 28, 2006, now Pat. No. 7,970,452, which is a continuation-in-part of application No. 10/916,738, filed on Aug. 12, 2004, now Pat. No. 7,379,769.

(60) Provisional application No. 60/506,784, filed on Sep. 30, 2003.

(51) Int. Cl.
| A61B 8/08 | (2006.01) |
| A61B 8/00 | (2006.01) |
| G01S 7/52 | (2006.01) |
| A61B 10/02 | (2006.01) |
| A61B 17/34 | (2006.01) |

(52) U.S. Cl.
CPC ............ *A61B 8/4245* (2013.01); *A61B 8/4416* (2013.01); *A61B 8/5238* (2013.01); *A61B 19/201* (2013.01); *A61B 19/203* (2013.01); *G01S 7/52049* (2013.01); *A61B 8/0833* (2013.01); *A61B 10/0233* (2013.01); *A61B 2017/3411* (2013.01); *A61B 2017/3413* (2013.01); *A61B 2019/205* (2013.01); *A61B 2019/5236* (2013.01); *A61B 2019/5276* (2013.01); *A61B 2019/5408* (2013.01)

(56) References Cited

U.S. PATENT DOCUMENTS

| | | |
|---|---|---|
| 4,552,346 A | 11/1985 | Schnelle et al. |
| 4,572,203 A | 2/1986 | Feinstein |
| 4,733,661 A | 3/1988 | Palestrant |
| 4,825,162 A | 4/1989 | Roemer et al. |
| 4,930,516 A | 6/1990 | Alfano et al. |
| 4,930,525 A | 6/1990 | Palestrant |
| 4,943,986 A | 7/1990 | Barbarisi |
| 4,989,608 A | 2/1991 | Ratner |
| 5,014,968 A | 5/1991 | Lammers et al. |
| 5,047,036 A | 9/1991 | Koutrouvelis |
| 5,072,721 A | 12/1991 | Weiler et al. |
| 5,096,216 A | 3/1992 | McCalla |
| 5,154,179 A | 10/1992 | Ratner |
| 5,196,019 A | 3/1993 | Davis et al. |
| 5,297,551 A | 3/1994 | Margosian et al. |
| 5,308,352 A | 5/1994 | Koutrouvelis |
| 5,426,685 A | 6/1995 | Pellegrino et al. |
| 5,548,218 A | 8/1996 | Lu |
| 5,569,266 A | 10/1996 | Siczek |
| 5,575,798 A | 11/1996 | Koutrouvelis |
| 5,590,653 A | 1/1997 | Aida et al. |
| 5,590,655 A | 1/1997 | Hussman |
| 5,594,337 A | 1/1997 | Boskamp |
| 5,678,549 A | 10/1997 | Heywang-Koebrunner et al. |
| 5,682,098 A | 10/1997 | Vij |
| 5,682,890 A | 11/1997 | Kormos et al. |
| 5,706,812 A | 1/1998 | Strenk et al. |
| 5,744,958 A | 4/1998 | Werne |
| 5,782,764 A | 7/1998 | Werne |
| 5,817,023 A | 10/1998 | Daft |
| 5,855,554 A | 1/1999 | Schneider et al. |
| 5,868,673 A | 2/1999 | Vesely |
| 5,868,757 A | 2/1999 | Koutrouvelis |
| 5,944,023 A | 8/1999 | Johnson et al. |
| 6,066,102 A | 5/2000 | Townsend et al. |
| 6,091,985 A | 7/2000 | Alfano et al. |
| 6,159,221 A | 12/2000 | Chakeres |
| 6,163,616 A | 12/2000 | Feldman |
| 6,163,717 A | 12/2000 | Su |
| 6,174,291 B1 | 1/2001 | McMahon et al. |
| 6,201,392 B1 | 3/2001 | Anderson et al. |
| 6,229,145 B1 | 5/2001 | Weinberg |
| 6,281,681 B1 | 8/2001 | Cline et al. |
| 6,295,671 B1 | 10/2001 | Reesby et al. |
| 6,298,506 B1 | 10/2001 | Heinold et al. |
| 6,302,579 B1 | 10/2001 | Meyer et al. |
| 6,324,243 B1 | 11/2001 | Edic et al. |
| 6,334,067 B1 | 12/2001 | Brabrand |
| 6,421,454 B1 | 7/2002 | Burke et al. |
| 6,421,553 B1 | 7/2002 | Costa et al. |
| 6,437,567 B1 | 8/2002 | Schenck et al. |
| 6,446,286 B1 | 9/2002 | Karmalawy |
| 6,459,923 B1 | 10/2002 | Plewes et al. |
| 6,498,489 B1 | 12/2002 | Vij |
| 6,521,209 B1 | 2/2003 | Meade et al. |
| 6,526,299 B2 | 2/2003 | Pickard |
| 6,591,128 B1 | 7/2003 | Wu et al. |
| 6,593,101 B2 | 7/2003 | Richards-Kortum et al. |
| 6,628,983 B1 | 9/2003 | Gagnon |
| 6,639,406 B1 | 10/2003 | Boskamp et al. |
| 6,640,364 B1 | 11/2003 | Josephson et al. |
| 6,675,037 B1 | 1/2004 | Tsekos |
| 6,697,652 B2 | 2/2004 | Georgakoudi et al. |
| 6,723,303 B1 | 4/2004 | Quay |
| 6,806,711 B2 | 10/2004 | Reykowski |
| 6,810,595 B2 | 11/2004 | Chan |
| 6,822,450 B2 | 11/2004 | Klinge et al. |
| 6,867,593 B2 | 3/2005 | Menon et al. |
| 6,904,305 B2 | 6/2005 | Tsekos |
| 6,922,859 B2 | 8/2005 | Gagnon et al. |
| 6,927,406 B2 | 8/2005 | Zyromski |
| 6,950,492 B2 | 9/2005 | Besson |
| 7,011,447 B2 | 3/2006 | Moyers |
| 7,020,314 B1 | 3/2006 | Suri et al. |
| 7,023,209 B2 | 4/2006 | Zhang et al. |
| 7,024,027 B1 | 4/2006 | Suri et al. |
| 7,024,711 B1 | 4/2006 | Stasney et al. |
| D533,278 S | 12/2006 | Luginbuhl et al. |
| 7,155,043 B2 | 12/2006 | Daw |
| 7,166,113 B2 | 1/2007 | Arambula et al. |
| 7,176,683 B2 | 2/2007 | Reeder et al. |
| 7,245,125 B2 | 7/2007 | Harer et al. |
| 7,245,694 B2 | 7/2007 | Jing et al. |
| D569,977 S | 5/2008 | Luginbuhl et al. |
| 7,373,676 B2 | 5/2008 | Markovic et al. |
| 7,379,769 B2 | 5/2008 | Piron et al. |
| 7,545,966 B2 | 6/2009 | Lewin et al. |
| 7,583,786 B2 | 9/2009 | Jing et al. |
| 7,656,993 B2 | 2/2010 | Hoernig |
| 7,711,407 B2 | 5/2010 | Hughes et al. |
| 7,809,426 B2 | 10/2010 | Kim et al. |
| 7,881,428 B2 | 2/2011 | Jing et al. |
| 7,908,690 B2 | 3/2011 | Luginbuhl et al. |
| 7,925,328 B2 | 4/2011 | Urquhart et al. |
| 7,937,132 B2 | 5/2011 | Piron et al. |
| 7,970,452 B2 | 6/2011 | Piron et al. |
| 8,050,736 B2 | 11/2011 | Piron et al. |
| 8,155,417 B2 | 4/2012 | Piron et al. |
| 8,162,847 B2 | 4/2012 | Wale et al. |
| 8,162,848 B2 | 4/2012 | Hibner et al. |
| 8,162,849 B2 | 4/2012 | Deshmukh et al. |
| 8,241,301 B2 | 8/2012 | Zhang et al. |
| 8,290,569 B2 | 10/2012 | Piron et al. |
| 8,292,824 B2 | 10/2012 | Okada |
| 8,298,245 B2 | 10/2012 | Li et al. |
| 8,560,051 B2 * | 10/2013 | Piron et al. ............... 600/411 |
| 8,571,632 B2 * | 10/2013 | Piron et al. ............... 600/411 |
| 8,744,550 B2 * | 6/2014 | Piron et al. ............... 600/415 |
| 2001/0011394 A1 | 8/2001 | Heimbrock et al. |
| 2001/0039378 A1 | 11/2001 | Lampman et al. |
| 2002/0035864 A1 | 3/2002 | Paltieli et al. |
| 2002/0056161 A1 | 5/2002 | Falbo et al. |
| 2002/0073717 A1 | 6/2002 | Dean et al. |
| 2002/0095730 A1 | 7/2002 | Al-Kassim et al. |
| 2002/0099264 A1 | 7/2002 | Fontenot |
| 2002/0131551 A1 | 9/2002 | Johnson et al. |

(56) References Cited

U.S. PATENT DOCUMENTS

| | | |
|---|---|---|
| 2002/0156365 A1 | 10/2002 | Tsekos |
| 2002/0164810 A1 | 11/2002 | Dukor et al. |
| 2002/0180442 A1 | 12/2002 | Vij |
| 2002/0193815 A1 | 12/2002 | Foerster et al. |
| 2003/0007598 A1 | 1/2003 | Wang et al. |
| 2003/0191397 A1 | 10/2003 | Webb |
| 2003/0194050 A1 | 10/2003 | Eberhard et al. |
| 2003/0199753 A1 | 10/2003 | Hibner et al. |
| 2003/0199754 A1 | 10/2003 | Hibner et al. |
| 2003/0206019 A1 | 11/2003 | Boskamp |
| 2004/0077972 A1 | 4/2004 | Tsonton et al. |
| 2004/0081273 A1 | 4/2004 | Ning |
| 2004/0183534 A1 | 9/2004 | Chan et al. |
| 2004/0216233 A1 | 11/2004 | Ludwig et al. |
| 2004/0220467 A1 | 11/2004 | Bonutti |
| 2005/0005356 A1 | 1/2005 | Zacharopoulos et al. |
| 2005/0033315 A1 | 2/2005 | Hankins |
| 2005/0059877 A1 | 3/2005 | Falbo |
| 2005/0080333 A1 | 4/2005 | Piron et al. |
| 2005/0104591 A1 | 5/2005 | Qu et al. |
| 2005/0228267 A1 | 10/2005 | Bulkes et al. |
| 2005/0267373 A1 | 12/2005 | Lee |
| 2006/0024132 A1 | 2/2006 | Seman |
| 2006/0026761 A1 | 2/2006 | Falbo |
| 2006/0122630 A1 | 6/2006 | Daum et al. |
| 2006/0133580 A1 | 6/2006 | Vezina |
| 2006/0221942 A1 | 10/2006 | Fruth et al. |
| 2006/0241408 A1 | 10/2006 | Yakubovsky et al. |
| 2007/0016003 A1 | 1/2007 | Piron et al. |
| 2007/0038144 A1 | 2/2007 | Hughes et al. |
| 2007/0039101 A1 | 2/2007 | Luginbuhl et al. |
| 2007/0050908 A1 | 3/2007 | Kogan et al. |
| 2007/0092059 A1 | 4/2007 | Eberhard et al. |
| 2007/0149878 A1 | 6/2007 | Hankins |
| 2007/0161935 A1 | 7/2007 | Torrie et al. |
| 2007/0167769 A1 | 7/2007 | Ikuma et al. |
| 2007/0233157 A1 | 10/2007 | Mark et al. |
| 2007/0238949 A1 | 10/2007 | Wang et al. |
| 2007/0255168 A1 | 11/2007 | Hibner et al. |
| 2007/0255170 A1 | 11/2007 | Hibner et al. |
| 2007/0276234 A1 | 11/2007 | Shahidi |
| 2008/0005838 A1 | 1/2008 | Wan Fong et al. |
| 2008/0033454 A1 | 2/2008 | Lukoschek et al. |
| 2008/0077005 A1* | 3/2008 | Piron et al. ............ 600/411 |
| 2008/0095421 A1 | 4/2008 | Sun et al. |
| 2008/0132785 A1 | 6/2008 | Piron et al. |
| 2008/0132912 A1 | 6/2008 | Shabaz |
| 2008/0216239 A1 | 9/2008 | Luginbuhl et al. |
| 2008/0230074 A1 | 9/2008 | Zheng et al. |
| 2008/0234569 A1 | 9/2008 | Tidhar et al. |
| 2008/0255443 A1 | 10/2008 | Piron et al. |
| 2008/0306377 A1 | 12/2008 | Piron et al. |
| 2009/0149738 A1 | 6/2009 | Piron et al. |
| 2009/0156961 A1 | 6/2009 | Tsonton et al. |
| 2009/0216110 A1 | 8/2009 | Piron et al. |
| 2009/0222229 A1 | 9/2009 | Kakinami |
| 2009/0247861 A1 | 10/2009 | Manus et al. |
| 2009/0270725 A1 | 10/2009 | Leimbach et al. |
| 2009/0275830 A1 | 11/2009 | Falco et al. |
| 2010/0041990 A1 | 2/2010 | Schlitt et al. |
| 2010/0249595 A1 | 9/2010 | Xu et al. |
| 2010/0280354 A1 | 11/2010 | Zhang et al. |
| 2010/0324445 A1 | 12/2010 | Mollere et al. |
| 2010/0324448 A1 | 12/2010 | Mollere |
| 2011/0034796 A1 | 2/2011 | Ma et al. |
| 2011/0134113 A1 | 6/2011 | Ma et al. |
| 2011/0152714 A1 | 6/2011 | Luginbuhl et al. |
| 2011/0153254 A1 | 6/2011 | Hartov et al. |
| 2011/0173753 A1 | 7/2011 | Luginbuhl et al. |
| 2012/0172704 A1 | 7/2012 | Piron et al. |
| 2013/0053684 A1 | 2/2013 | Piron et al. |

FOREIGN PATENT DOCUMENTS

| | | |
|---|---|---|
| EP | 0396866 A2 | 11/1990 |
| EP | 0753758 A1 | 1/1997 |
| EP | 2445413 A1 | 5/2012 |
| EP | 2503934 A1 | 10/2012 |
| WO | 9608199 A1 | 3/1996 |
| WO | 01/28412 A1 | 4/2001 |
| WO | 02/39135 A2 | 5/2002 |
| WO | 2006017172 A1 | 2/2006 |
| WO | 2007070285 A2 | 6/2007 |
| WO | 2008064271 A2 | 5/2008 |
| WO | 2010078048 A2 | 7/2010 |
| WO | 2010148503 A1 | 12/2010 |
| WO | 2011014966 A1 | 2/2011 |
| WO | 2011134113 A1 | 11/2011 |
| WO | 2013001377 A2 | 1/2013 |

OTHER PUBLICATIONS

International Search Report for International Application No. PCT/CA2010/001228 mailed Oct. 2, 2011, 5 pages.

European Search Report for European Patent Application No. 07800538.6 mailed Mar. 1, 2012, 8 pages.

Piron, Cameron A., Hybrid Imaging Guidance System for Biopsy of the Breast, Thesis Paper, University of Toronto, 2001.

Palmer, Gregory, et al., "Optimal Methods for Fluorescence and Diffuse Reflectance Measurements of Tissue Biopsy Samples," Lasers in Surgery and Medicine, 30:191-200 (2002).

Kline, Nicole, et al., "Raman Chemical Imaging of Breast Tissue," Journal of Raman Spectroscopy, vol. 28, 119-124 (1997).

Manoharan, Ramasamy, et al., "Histochemical Analysis of Biological Tissues Using Raman Spectroscopy," Spectrochimica Acta Part A.52 (1996) 215-249.

Shafer-Peltier, K.E. et al. "Raman Microspectroscopic Model of Human Breast Tissue: Implications for Breast Cancer Diagnosis in Vivo" Journal of Raman Spectroscopy V.33 (2002).

Ntziachristos V., et al. "Concurrent MRI and Diffuse Optical Tomography of Breast After Indocyanine Green Enhancement," PNAS, Mar. 14, 2000, vol. 97, No. 6, 2767-2772.

Buadu, LD, et al., Breast Lesions: Correlation of Contrast Medium Enhancement Patterns on MR Images with Histopathologic Findings and Tumor Angiogenesis.

Kriege, M., et al., "Efficacy of MRI and Mammography for Breast-Cancer Screening in Women with Familial or Genetic Predisposition," N Engl J Med 351:427-437 (2004).

Non-Final Office Action mailed Feb. 9, 2007 in U.S. Appl. No. 10/916,738.

Response to Feb. 9, 2007 Office Action in U.S. Appl. No. 10/916,738, Jul. 11, 2007.

Non-Final Office Action mailed Sep. 24, 2007 in U.S. Appl. No. 10/916,738.

Response to Sep. 24, 2007 Office Action in U.S. Appl. No. 10/916,738, Dec. 26, 2007.

Non-Final Office Action mailed Nov. 16, 2009 in U.S. Appl. No. 11/442,944.

Response to Nov. 16, 2009 Office Action in U.S. Appl. No. 11/442,944, May 17, 2010.

Non-Final Office Action mailed May 12, 2009 in U.S. Appl. No. 12/031,271.

Response to May 12, 2009 Office Action in U.S. Appl. No. 12/031,271, Nov. 12, 2009.

Final Office Action mailed Feb. 5, 2010 in U.S. Appl. No. 12/031,271.

Response to Feb. 5, 2010 Office Action in U.S. Appl. No. 12/031,271, Aug. 5, 2010.

Non-Final Office Action mailed Jan. 22, 2010 in U.S. Appl. No. 11/447,053.

Response to Jan. 22, 2010 Office Action in U.S. Appl. No. 11/447,053, Jul. 22, 2010.

International Search Report mailed Dec. 13, 2007 in International Application No. PCT/CA2007/001513.

International Preliminary Report on Patentability issued Mar. 3, 2009 in International Application No. PCT/CA2007/001513.

(56) References Cited

OTHER PUBLICATIONS

European Search Report mailed Jul. 30, 2009 in EP Application No. 09007010.3.

European Search Report mailed Oct. 16, 2009 in EP Application No. 09007010.3.

General Electric—Press Release—"GE Healthcare Introduces Ultrasound Fusion; New LOGIQ E9 Merges Real-time Ultrasound with CT, MR and PET," Sep. 2, 2008, 2 pages.

International Preliminary Report of Patentability for International Application No. PCT/CA2010/001871 dated May 30, 2012, 1 page.

International Search Report and Written Opinion of the International Searching Authority for International Application No. PCT/CA2010/001871 dated Mar. 8, 2011, 9 pages.

M. Berger, "Image Fusion and Needle Guidance in Ultrasound", General Electric, Power Point Presentation, date unknown, 17 pages.

P. Mullen and C. Owen, "MR, Ultrasound Fusion: Bridging the Gap Between Clinical Benefits, Access and Equipment Utilization," SignaPULSE—A GE Healthcare MR Publication, Spring 2009, 5 pages.

Update of AAPM Task Group No. 43 Report: A revised AAPM protocol for brachytherapy does calculations; Med. Phys. vol. 31 No. 3, Mar. 2004; pp. 633-674.

Supplement to the 2004 update of the AAPM Task Group No. 43 Report; Med. Phys. vol. 34 No. 6, Jun. 2007; pp. 2187-2206.

Erratum: "Update of AAPM Task Group No. 43 Report: A revised AAPM protocol for brachytherapy dose calculations" [Med. Phys. 31, 633-674 (2004)].

International Preliminary Report on Patentability for PCT/CA10/000973, dated Jan. 4, 2012.

International Search Report for International Application No. PCT/CA2010/000973, mailed Oct. 1, 2010, 3 pages.

Pagoulatos et al., "Interactive 3-D Registration of Ultrasound and Magnetic Resonance Images Based on a Magnetic Position Sensor," IEEE Transactions on Information Technology in Biomedicine, vol. 3, No. 4, Dec. 1999, 11 pages.

\* cited by examiner

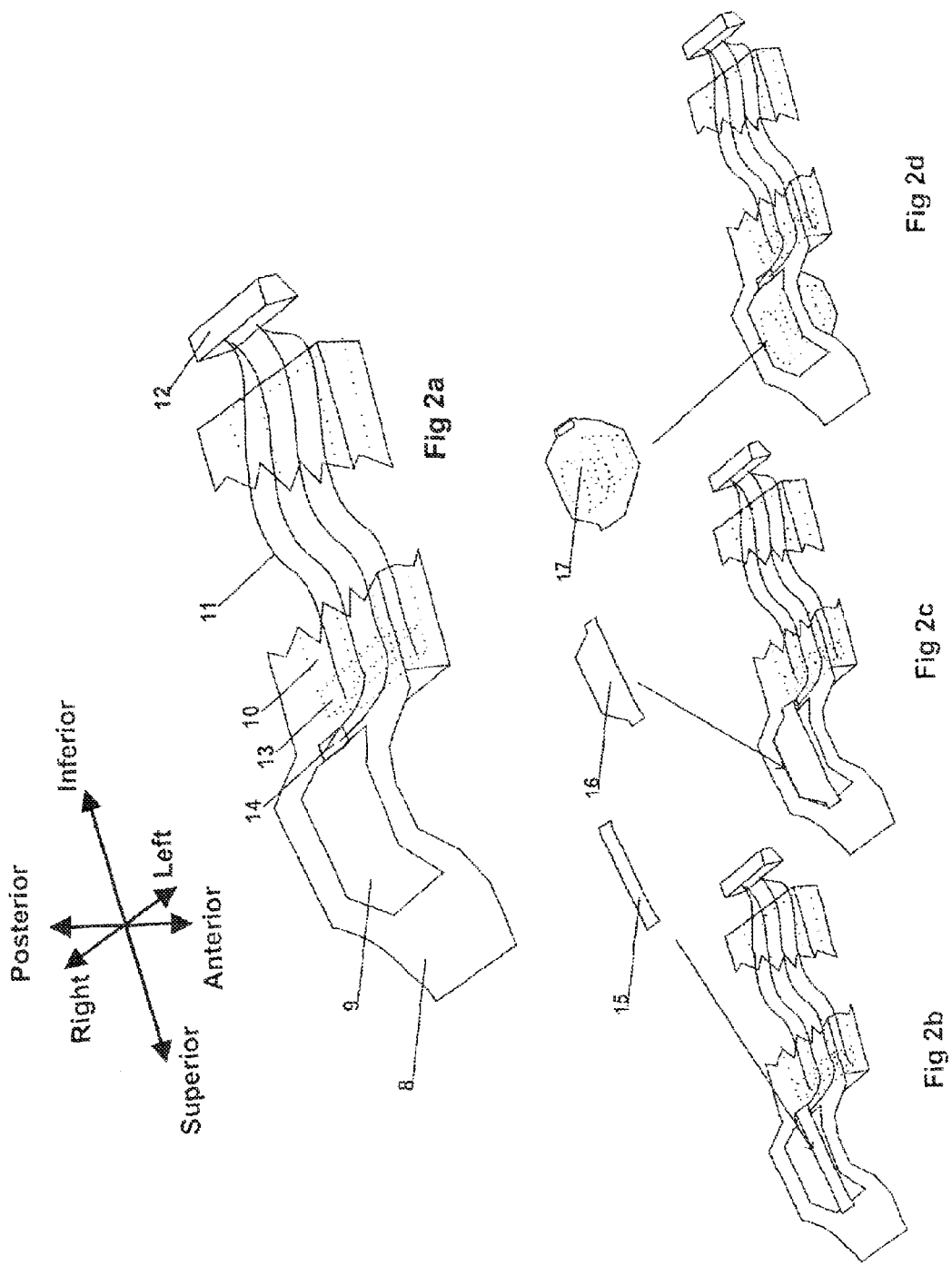

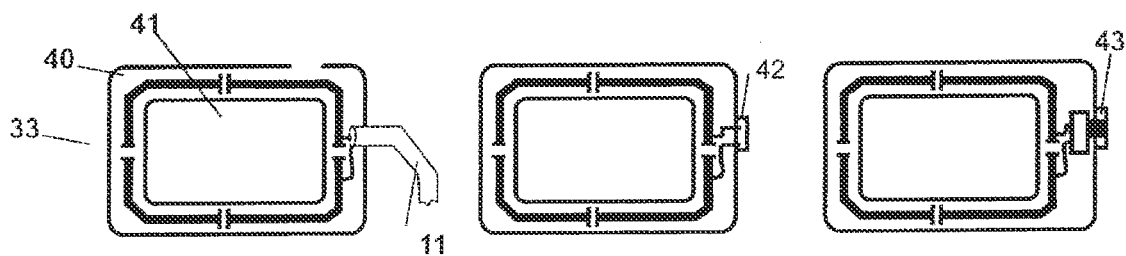
Fig 5a   Fig 5b   Fig 5c
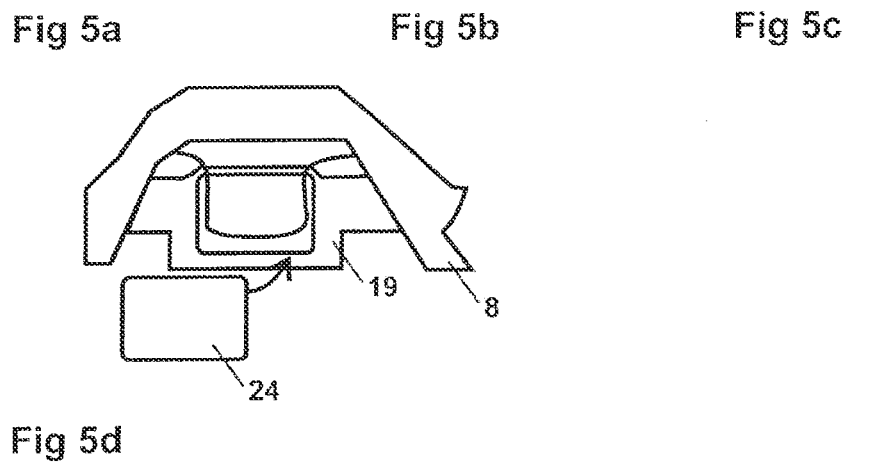
Fig 5d
Fig 5e
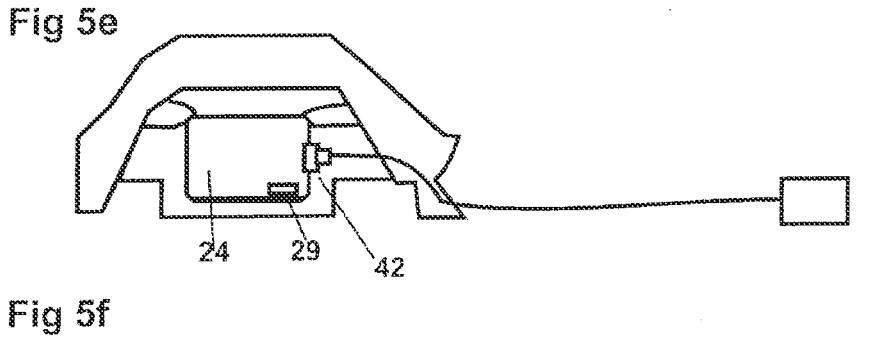
Fig 5f
Fig 5g

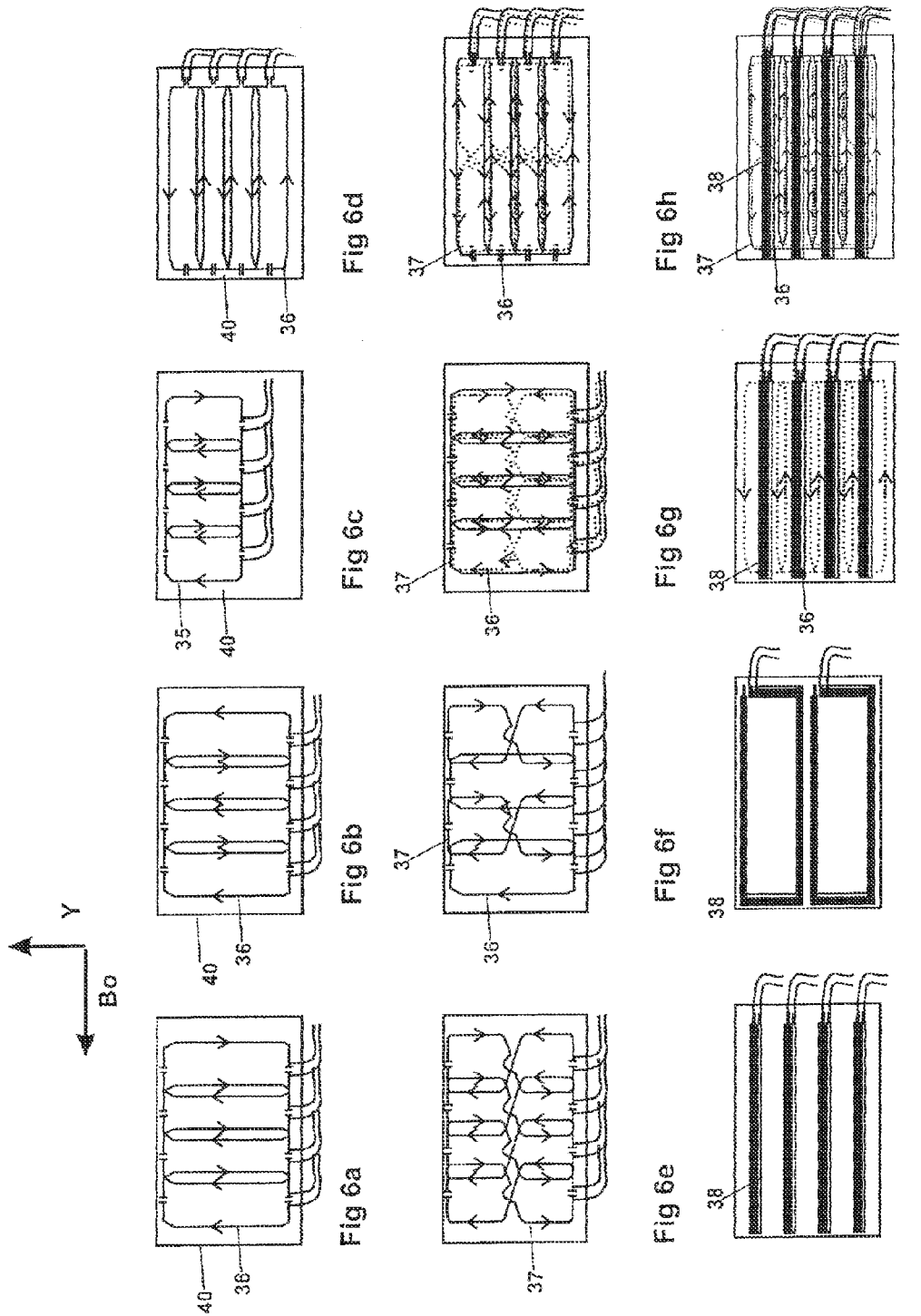

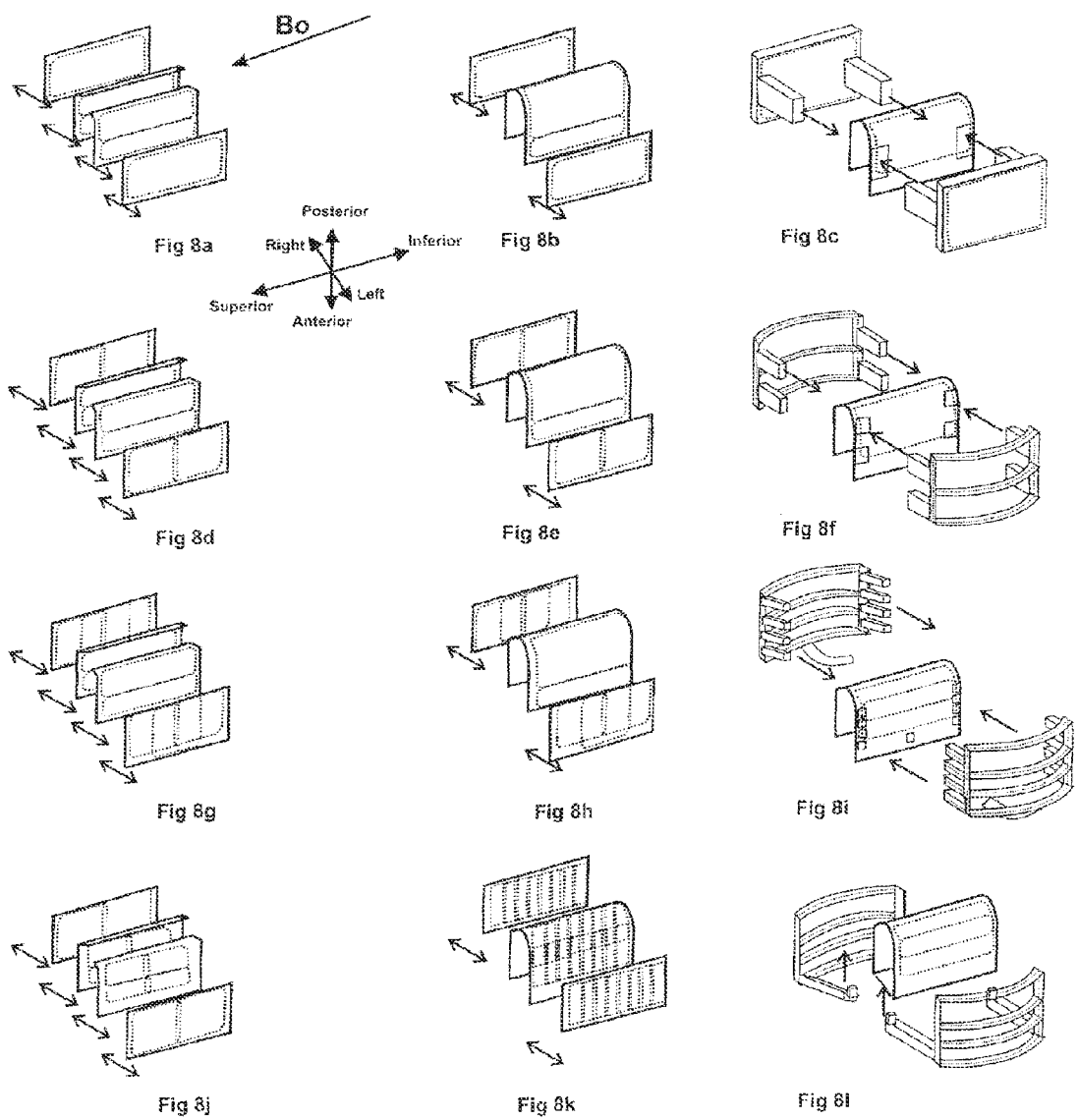

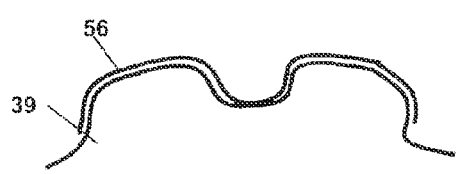
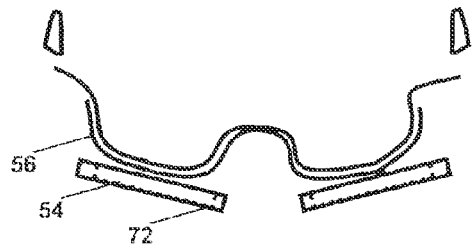
Fig 10a    Fig 10b
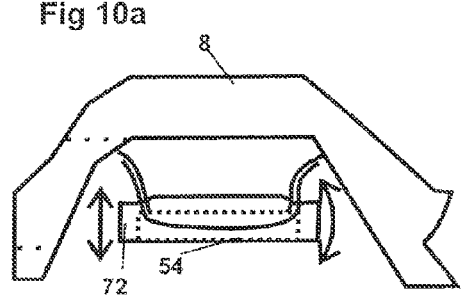
Fig 10c
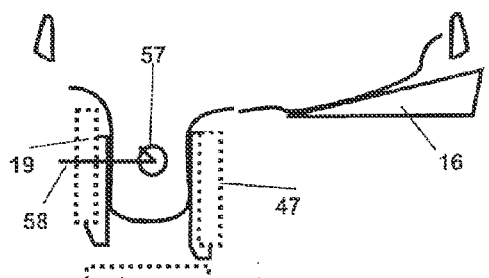
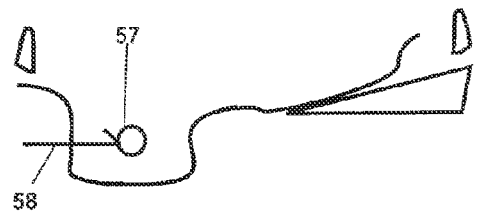
Fig 10d    Fig 10e
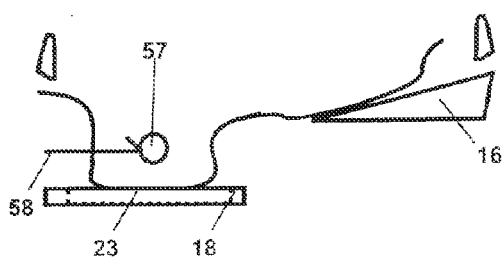
Fig 10f

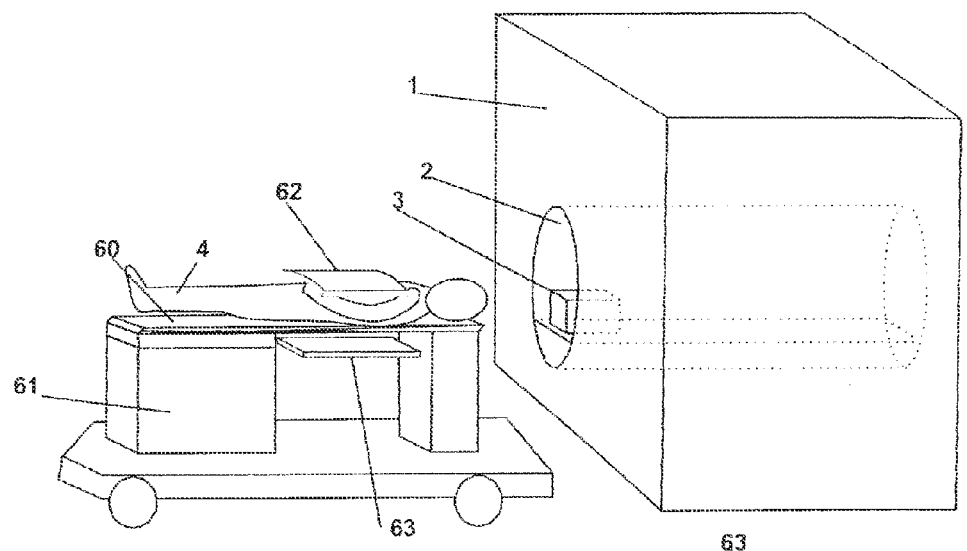
Fig 11a
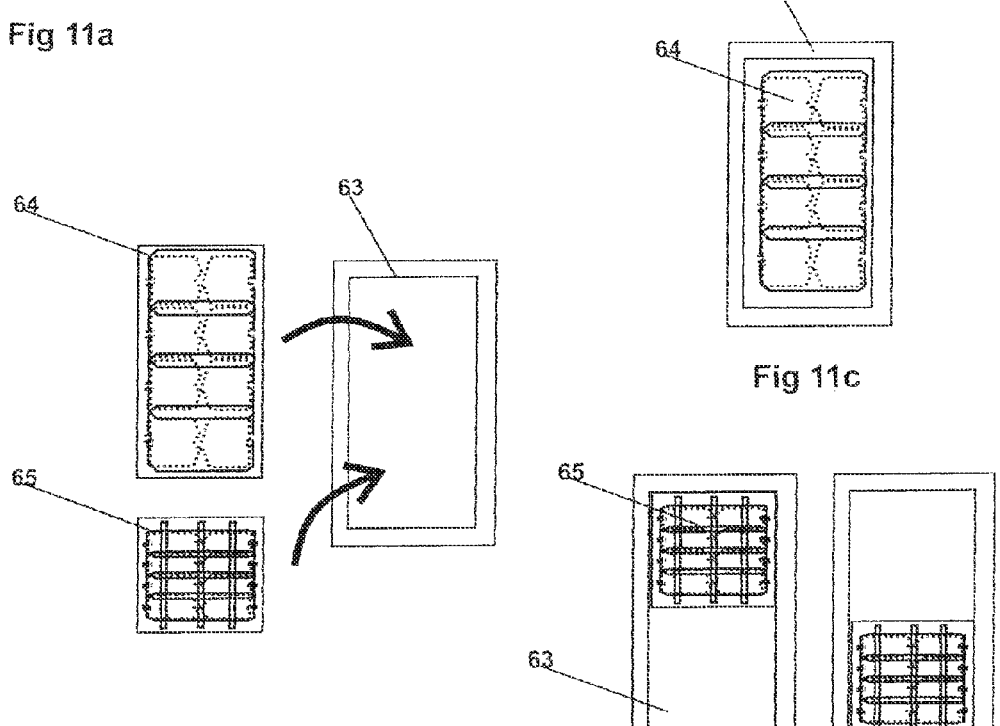
Fig 11b
Fig 11c
Fig 11d

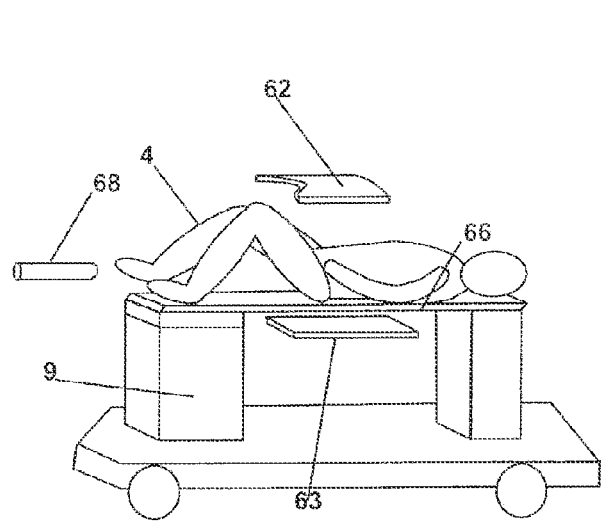
Fig 12a
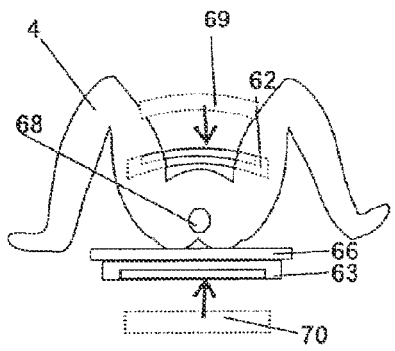
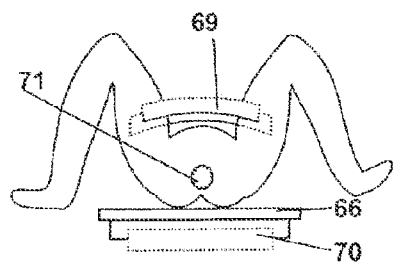
Fig 12b
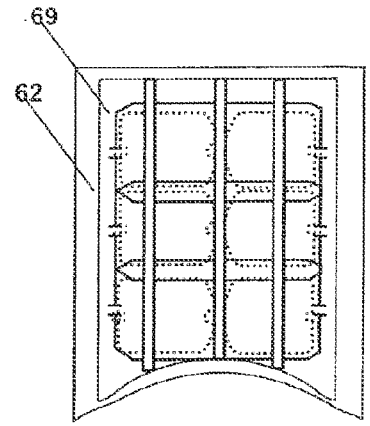
Fig 12c
Fig 12d
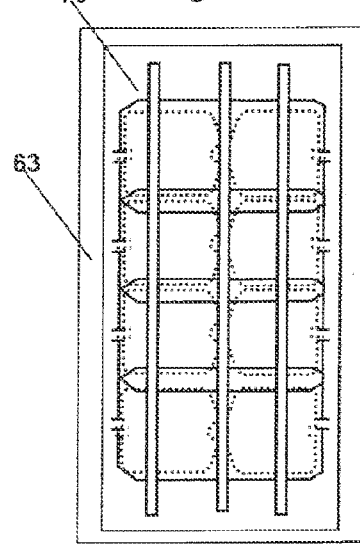
Fig 12e

OPEN ARCHITECTURE IMAGING APPARATUS AND COIL SYSTEM FOR MAGNETIC RESONANCE IMAGING

CROSS-REFERENCE TO RELATED APPLICATION

This application is a continuation of and claims priority to U.S. patent application Ser. No. 12/139,123, filed on Jun. 13, 2008, entitled "OPEN ARCHITECTURE IMAGING APPARATUS AND COIL SYSTEM FOR MAGENTIC RESONANCE IMAGING :"(issued as U.S. Pat. No. 8,571,632), which is a continuation of and claims priority to U.S. patent application Ser. No. 11/442,944, filed Aug. 28, 2006 (issued as U.S. Pat. No. 7,970,452), which is a continuation-in-part of and claims priority to U.S. patent application Ser. No. 10/916,738, filed Aug. 12, 2004, titled HYBRID IMAGING METHOD TO MONITOR MEDICAL DEVICE DELIVERY AND PATIENT SUPPORT FOR USE IN THE METHOD (issued as U.S. Pat. No. 7,379,769), which in turn claims priority from U.S. Provisional Application No. 60/506,784, filed Sep. 30, 2003; this application is also a continuation of and claims priority to U.S. patent application Ser. No. 13/112,208, filed May 20, 2011, entitled "OPEN ARCHITECTURE IMAGING APPARATUS AND COIL SYSTEM FOR MAGENTIC RESONANCE IMAGING" (issued as U.S. Pat. No. 8,560,051), which is a continuation of and claims priority to U.S. patent application Ser. No. 11/442,944, filed Aug. 28, 2006 (issued as U.S. Pat. No. 7,970,452) which is a continuation-in-part of and claims priority to U.S. patent application Ser. No. 10/916,738, filed Aug. 12, 2004, titled HYBRID IMAGING METHOD TO MONITOR MEDICAL DEVICE DELIVERY AND PATIENT SUPPORT FOR USE IN THE METHOD (issued as U.S. Pat. No. 7,379,769), which in turn claims priority from U.S. Provisional Application No. 60/506,784, filed Sep. 30, 2003, each of which applications are incorporated herein by reference in their entirety.

FIELD OF THE INVENTION

The present invention relates to magnetic resonance imaging (MRI), in particular to an open architecture patient support system with embedded and separable radio frequency coils and their method of positioning for the use in magnetic resonance imaging and spectroscopy.

BACKGROUND OF THE INVENTION

Magnetic resonance imaging (MRI) detects the faint nuclear magnetic resonance (NMR) signals given off by protons in the presence of a strong magnetic field after excitation by a radio frequency signal. The NMR signals are detected using antennae termed "coils". The term "coil" is also commonly used to refer to the antenna(e) and its housing or support structure. Thus "coil" may refer to a structure that contains a number of coils. "Coil element(s)" is used to refer to the electrical part of the device, the radio frequency coil or antennae.

NMR signals are extremely faint. Sensitivity of a coil to these signals decreases rapidly with increasing distance between the coil and the volume of interest. Coils such as FIG. 8, or butterfly coils, solenoid coils, volume coils, and surface coils are therefore placed in close proximity to the region of interest of the imaged object. The size of the local coils is kept small to allow them to be easily fit to the patient on the MRI patient table and to enable imaging of only the imaging volume of interest, since imaging regions that are not required adds noise to the acquired signal unnecessarily. Coils local to the anatomy of interest tend to have a higher signal-to-noise ratio (SNR) than larger coils such as a "body coil" which is useful for obtaining large survey scans of the patient.

The smaller the size of the local coil, the smaller its field of view, or sensitivity profile. Imaging of larger areas using the smaller coils requires the use of multiple small coils, either simultaneously in a combined manner or by moving the coil between imaging acquisitions. Coils can be operated individually, as multiple coils in a phased array, circularly polarized or in quadrature mode. Combining signals from multiple coils can yield improvements in SNR. Part of the challenge associated with using multiple coils for imaging is the fact that the fields of individual coils may interact, resulting in coil-to-coil coupling, where these interactions serve to reduce the coil quality factor, or Q. In the prior art various patents have been presented whose proposed objective is to reduce this coupling. One technique for reducing the coil-to-coil coupling of a multi-coil array is to overlap adjacent coils by approximately 10% of their area, such that their additional field contributions cancel resulting in no coupling. In cases where there may be more than 2 coils, the process of decoupling by overlapping can be complicated, as coil coupling may occur between non-nearest neighbors in which the field cancellations are complicated significantly. In these cases, coupling can be reduced through the addition of capacitors, inductors or additional circuits between coils which experience some amount of coupling. Low-impedance preamplifiers may be added to the coil system which can reduce the effects of coil coupling. In much of the prior art, combinations of these various techniques have been described and employed successfully.

Furthermore, operating a coil as a receive-only coil requires that the coil is blocked, or uncoupled from the magnet body coil while the body coil or other coils are acting in transmit, or excitation mode. Again, various patents are presented in the prior art that seek to improve upon this process.

A further consideration with coil systems is their ability to operate in a parallel imaging mode. In these modes of operation, imaging techniques such as SMASH, SENSE, PILS or GRAPPA, require coils to be imaging independent volumes. Based on the sensitivity profiles of these coils operating independently, a reconstruction algorithm can be implemented that enables reconstruction of a full image volume in a fraction of the conventional image acquisition time. Coils should image independent volumes for optimal parallel imaging, and therefore decoupling strategies that employ overlapping of coils are non optimal.

An additional consideration with coil technologies and generally with MRI systems is the push towards higher and higher numbers of simultaneous imaging channels. Coil systems are routinely implemented in 8-channel systems utilizing eight separate antennas, but some systems currently implement up to 96 channels, with higher numbers of channels being planned. The benefits of additional channels include higher acceleration factors from parallel imaging implementations, and smaller coils for higher signal to noise ratios. With this constant drive to upgrade MRI systems, legacy coil systems become obsolete. There is currently no way of upgrading the number of channels associated with a coil without buying an entire coil apparatus which includes the main structure, the coil circuitry and the connection to the MRI.

Coils must be tuned to the Larmor frequency associated with the magnet field strength in which it is meant to operate, i.e. 1.5 T requires a coil tuned to 63.86 MHz, 3.0 T requires 127.7 MHz. In most commercial coils, the coil elements or antenna are inseparable from the patient support structure, or are inseparable from the coil housing. For each MRI having a different field strength, therefore, a new coil system, consisting of the coil elements, coil housing, patient support (if any) and cabling is required.

Although most MRI imaging is concerned with signals from hydrogen atoms, other nuclei (e.g. CI3K, P, Na) are sometimes of interest for MR spectroscopy or imaging. Traditionally, the low signal to noise ratio associated with measurement of these nuclei have precluded their use for any practical clinical imaging. However, with the advent of improved coil technologies and higher field strengths, these techniques are becoming more practical. However, coils tuned to the appropriate precessional (Laramor) frequencies of the nuclei are required as well as the associated circuitry to enable acquisition of these signals on the limited bandwidth of standard MRI systems. There are some systems that are appropriate for double tuned imaging (i.e. hydrogen in combination with another species), however there are limitations associated with integrating these multiple coils into one coil housing.

Furthermore, coil switching, multiplexing, or dynamic coil selection strategies enable activation and inactivation of sets of coils from a larger coil array set. This strategy can be used to optimize a subset of coils for imaging of anatomies of a smaller volume, or to switch between areas of interest during the image acquisition or imaging procedure. For this strategy to be accommodated, the set of coils, or subset of these coils must be appropriately designed. There currently are no systems which accommodate this type of imaging strategy with a modular coil system design.

Another consideration for imaging, particularly of the human breast, is the varying positions in which the breast is imaged for MRI, US and mammography and in which surgical interventions may be performed. As the breast may often be imaged in the prone position for MRI while surgery and ultrasound (US) imaging examinations are performed almost exclusively in the supine position, it is difficult to correlate anatomical features between these positions. MR imaging of the breast in the supine position is very difficult and has not been accomplished with any degree of success.

As coil technology complexity and clinical demands continue to increase, a new strategy for coil systems is needed. A system is required that permits sizing coils appropriate to the anatomy, maximizes the number of coils used, providing coils tuned for different field strengths and nuclei, optimizes parallel imaging configurations, as well as providing an upgrade path for accommodating greater numbers of imaging channels.

SUMMARY OF THE INVENTION

This invention relates to the field of medical imaging and particularly to MRI radio-frequency coil arrangements and the corresponding supporting apparatus used to image human tissues. Fundamental to this invention is the ability to separate the coil elements (antennas) from the patient supporting system such that various Radiofrequency (RF) coil elements can be attached and/or selected for imaging. This concept is applied to traditional "tabletop" coils (i.e. coils which are placed on top of a general purpose MR imaging tabletop) and to dedicated stretchers having specialized tabletops that integrate coil elements. Means are presented for optimizing the use of said coils by enabling positioning, support, immobilization or compression of the anatomy of interest. Additionally, various RF antenna and circuit configurations appropriate to imaging in these imaging configurations are presented.

The prior art is focused on 1) specific fixed coil geometries for a dedicated purpose (head coil, cardiac coil, breast coil), or 2) separable coil arrangements when a set of generic coils can be arranged to image a general anatomy, or 3) arrangements where all the coils required to image the entire body are provided all in one system in which subsets can be deactivated, 4) or a set of coils that can be assembled to image various anatomies. In no case does the prior art focus on a singular anatomy and related structures and therefore do not provide for specialized applications required for that anatomy and related structures. i.e. have sets of coils adapted to fit different imaging needs with that anatomy, i.e. many sets of breast coils (some for high SNR, some for parallel imaging, some for interventions, some sized to smaller patients, some for spectroscopic applications), and the distinction is not made between a various aspects that make up a coil (the electronics, the coil housing-physical support for the electronics).

A desirable element of the present technology is the capability of providing a patient support structure in combination with the coil. In the use of a stable, secure and robust support, the coils may be removed and replaced (e.g., with coils having different field geometries as well as for repair) without disturbing the patient.

The benefits of a coil system separable from its housing or patient support structure include the ability to 1) configure a combined Field of View (FOV) optimized for the patient anatomy, 2) make use of all available receive channels and concentrate them on imaging only the desired field of view, 3) permit repositioning, replacing or removing coil elements without moving the patient such that openings are created for image-guided interventions, 4) use coil elements intended for higher or lower field strength or different nuclei, 5) deliver separable transmit and receive coil elements having different geometries, 6) provide for coil and compression arrangements that are optimized for positioning tissues (such as the breast) in various arrangements to facilitate and aid in subsequent imaging or surgical procedures, 7) allow different coil configurations to be made available to a physician without the need for separate support structures for each configuration, or 8) upgrade coil elements with new or enhanced functionality without the need to replace the entire assembly.

A significant aspect of this invention is that a separable and reconfigurable coil system enables coil configurations that may be optimized for a particular imaging purpose such as (in the breast) bilateral imaging, unilateral imaging, imaging of the chest wall for mastectomy or partial mastectomy patients, interventional procedures, high-field imaging or multi-nuclear imaging. Further to this invention are techniques for coupling the coil signals to the MRI scanner for data acquisition. Further still are specific coil geometries optimized for bilateral imaging and unilateral imaging in both receive-only and transceive imaging applications (transmit and receive). Additionally, these coil systems are designed to be used in parallel imaging applications such as SENSE and SMASH, in transmit, receive or transceive modes. Additionally, the coil systems may be operated in a transmit SENSE, or T-SENSE implementation where an array of coils can be used in coordination with parallel imaging applications.

Coil elements can be arranged in unique arrangements to reduce coil-to-coil coupling, to position a large number of coils close to the imaging volume and to maximally cover the volume of interest within the context of a modular coil system.

According to one aspect, a patient support and imaging system for a patient is provided. The patient support and imaging system comprises a main support structure configured to support an anatomy of a patient; a first component support structure moveably connected to the main support structure, wherein the first component support structure is configured to position a patient's tissue in a position for imaging; and a first RF coil system configured to be received and releasably attached to the first component support structure so that first RF coil system is positioned adjacent to the patient's tissue; wherein the first component support structure is configured to receive and release the first RF coil system. In one embodiment, the first component support structure is configured to position the first RF coil system adjacent to the patient's breast tissue. In one embodiment, the first component support structure is configured to provide a plurality of compression configurations for the patient's breast tissue.

In one embodiment, the first component support structure comprises at least one locking component to lock the first component support structure in position. In one embodiment, the first component support structure is configured to move along an anterior-posterior plane. In one embodiment, the first component support structure is configured to move along a medial-lateral plane. In one embodiment, the main support structure comprises at least one track constructed and arranged along the medial-lateral plane, and wherein the first component support structure is moveably coupled to the track. In one embodiment, the first RF coil system comprises a medial RF coil held by the first component support structure. In one embodiment, the first RF coil systems comprises a lateral RF coil held by the first component support structure. In one embodiment, the first component support structure is configured to provide unilateral imaging of one of a patient's breasts.

In one embodiment, the system further comprises a second component support structure configured to receive a second RF coil, wherein the first RF coil is a lateral coil and the second RF coil is a medial coil held by respective first and second component support structures. In one embodiment, the respective component support structures are configured to lock in a position adjacent to tissue for imaging. In one embodiment, the respective component support structures are configured to be positioned for bilateral imaging of the tissue. In one embodiment, the first component support structure is configured to receive and release at least one of an interventional and a guidance device. In one embodiment, the interventional device is configured to provide at least one access aperture for interventional procedures on patient's tissue.

According to one aspect, a method for MRI imaging a patient is provided. The method comprises accepting a patient's tissue to be imaged into a main support structure; holding a first RF coil system with a first component support structure moveably attached to the main support structure; moving the first component support structure and first RF coil system relative to the main support structure into a position adjacent to the patient's tissue to be imaged thereby defining a first imaging configuration; and imaging, with an MRI imager, the patient's tissue with the first component support structure and the first RF coil system in the first imaging configuration. In one embodiment, the method further comprises an act of locking the first component support structure and first RF coil system into the first imaging position for imaging.

In one embodiment, the method further comprises providing a second component support structure housing a second RF coil system to define a second imaging configuration. In one embodiment, the method further comprises moving at least one of the component support structures having a respective RF coil system to define the second imaging configuration. In one embodiment, the method further comprises imaging the patient's tissue according to the second imaging configuration. In one embodiment, the method further comprises housing at least one of an interventional device and a guidance device to the component support structure. In one embodiment, the method further comprises providing at least one access aperture with the interventional device for accessing the patient's tissue while in imaging position.

BRIEF DESCRIPTION OF THE DRAWINGS

FIG. 2—A. Shows a patient support structure for breast imaging without secondary support structures, compression plates or coils. The cables shown attach the various connection panels and ports on the support structure to the MRI connector. B. Shows the patient support structure with a sternum support attached. C. Shows the patient support structure with a contralateral breast support attached. D. Shows the patient support structure with a bilateral breast support attached.

FIG. 6—Shows various arrangements of coils integrated into a single arrangement. A. Shows four loop coils B. Shows four loop coils with alternating field directions. C. Shows four small loop coils. D. Shows four loop coils in a horizontal arrangement. E. Shows four butterfly coils F. Shows a combination of two loop and two butterfly coils. G. Shows four loop coils superimposed on four butterfly coils. H. Shows four loop/butterfly coils in a horizontal orientation. I. Shows four transmission line coils. J. Shows two transmission line coils presented as hybrid loops. K. Shows four overlapped transmission line and loop coils. L. Shows four sets of overlapped transmission line, loop and butterfly coils.

FIG. 8—Shows various coil arrangements for bilateral imaging applications. A. Shows bilateral coil plates with loop coils laterally and butterfly coils medially. B. Shows loop lateral coils and butterfly medial coils with the medial coils on a fixed medial structure. C. Shows loop lateral and butterfly medial coils with the medial coils on a fixed structure and the two lateral coils attaching in a fixed manner to the medial structure. D. Shows the same configuration as A, with two lateral coils decoupled from each other through overlapping E. Shows the same configuration as B, with two lateral coils decoupled from each other through overlapping Here the medial butterfly has none-symmetric lobes so as to better decouple with the lateral coil when positioned in a more posterior location. F. Shows the same configuration as C, with two lateral coils housed in an open coil housing, with two medial coils decoupled from each other through overlapping. G. Shows the same configuration as D, with three lateral coils decoupled from each other through overlapping H. Shows the same configuration as E, with three lateral coils decoupled from each other through overlapping. I. Shows the same configuration as F, with lateral coils housed in an open coil housing, with two medial coils decoupled from each other through overlapping. Here an anterior connection is provided for lateral and medial coil connection. J. Shows the same configuration as G, with two lateral coils decoupled from each other through overlapping and two medial coils decoupled through overlapping. K. Shows the same configuration as H, with eight lateral coils decoupled from each other through overlapping and eight medial coils decoupled through overlapping. L. Shows a similar configuration as I, with lateral coils housed in an open coil housing, with two medial coils decoupled from each other through overlapping. Here connection is performed from the anterior position.

FIG. 10—Shows various compression arrangements provided for an open architecture breast imaging system. A. Shows a patient in a supine position with a conformal immobilization plate. B. Shows the same patient in a prone position with the same immobilization plate in place. C. Shows b. in the sagittal plane. D. Shows an axial view of a breast after a localization wire has been inserted into a tumor. E. Shows the same patient after immobilization devices have been removed. F. Shows the breast compressed from the anterior direction.

FIG. 11—A. Shows a patient lying supine on a dedicated body imaging tabletop used with a dedicated stretcher. The stretcher is shown in-front of a closed bore MRI system. B. Shows a posterior support plate with various coil inserts. C. Shows a posterior support plate with a large FOV coil inserts. D. Shows how a set of coils can be placed in various positions within the support plate to allow for optimal positioning relative to the anatomy of interest.

FIG. 12—A. Shows a patient lying supine on a dedicated prostate imaging tabletop on a dedicated stretcher. B. Shows an axial view of the patient. C. Shows an anterior support plate with coil insert. D. Shows a prostate sheath with coil insert. E. Shows a posterior support plate with coil insert.

The foregoing features, objects and advantages of the present invention will be apparent to one generally skilled in the art upon consideration of the following detailed description of the invention.

DETAILED DESCRIPTION OF THE PREFERRED EMBODIMENT

The following described technology encompasses a method to improve magnetic resonance imaging through use of improved coil systems, associated support structures and apparatus. The preferred embodiments are described by reference to both the general and specific attributes and features of the components of the technology. However, this specification discloses only some specific embodiments as examples of the present technology, which as not intended to be limiting in the interpretation of the scope of the claimed invention of this patent. It will be readily apparent that numerous variations and modifications may be effected without departing from the true spirit and scope of the novel concepts of the invention.

This disclosure of technology includes RF coil designs, mechanical system designs and methods of configuring said coils so as to maximize signal arising from said system and enable imaging of anatomy in conformations not previously provided for. In the exemplary case this is described for breast imaging.

A fundamental aspect to this disclosure of technology is the separation of patient support structures from the RF coil system. This is embodied in either a dedicated stretcher with dedicated tabletop system (FIG. 1B) or the traditional tabletop system (FIG. 1A) for use in an MRI(1).

Figure 1A:
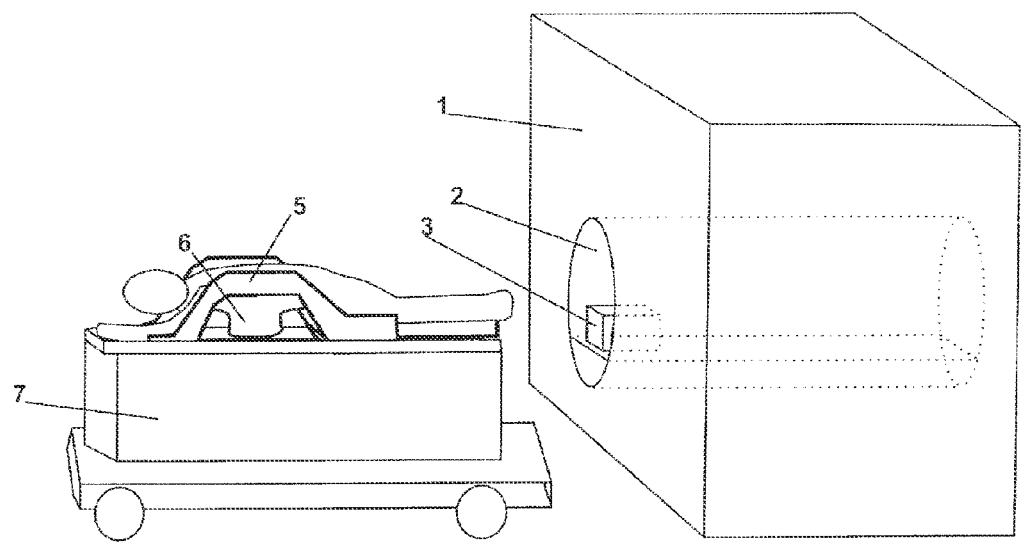
FIG. 1—A. Shows a patient lying prone on a tabletop breast coil on top of a standard patient transport stretcher. The stretcher is shown in front of a closed bore MR Imaging system. B. Shows a patient lying prone on a dedicated breast imaging tabletop on a dedicated stretcher. The stretcher is shown in front of a closed bore MRI system. C. Shows a specialized stretcher with tabletop in the undocked position relative to the MRI. D. Show the tabletop attached to the magnet and with cables automatically connected. E. Shows the tabletop with vertically disposed cable connection points. F. Shows this vertical tabletop attached to the MRI. G. Shows the stretcher containing cable connection points, H. Shows the stretcher attached to the MRI with the cable connections automatically connected during docking.

As shown in FIG. 1A the patient (4) lies prone, with feet first into the MRI bore (head first may work as well) (2) in preparation for MRI breast imaging. Presented in the Prior Art are a series of table top coil system designs for breast imaging in which the RF system is integrated into and is inseparable from the mechanical structure of the apparatus. Typically a tabletop coil system (5) is placed on top of an MRI's stretcher and general purpose tabletop and, in the case of breast imaging, the patient lies prone atop this structure. In the case of a cylindrical magnet of the style produced by General Electric, a patient transport stretcher is used to attach to the magnet. The stretcher (7) is typically a wheeled stretcher which can mechanically attach (dock) to the magnet (1). The general purpose tabletop is used to roll the patient into the magnet bore (2) and moves relative to the stretcher. The tabletop is driven in and out of the magnet by various mechanisms. In the case of the cylindrical magnet of the style produced by Siemens, a cantilevered patient support that is separable from the magnet is used. For Philips or Toshiba cylindrical magnets, a removable patient support is introduced by a different type of transport stretcher. The implementations provided by all of these magnet manufacturers are not designed to accommodate a specialized imaging or intervention application or special patient positioning and therefore consist of a simple flat tabletop. In order to tailor the MRI's imaging capability for a particular anatomy a dedicated coil system attached to a special purpose tabletop which sits on top of the transport stretcher is used. An example of such a proposed arrangement is presented in FIG. 1A.

The electronics housed in these coil systems are electrically connected to the MRI RF acquisition system. Various methods of attaching to the MRI system have been proposed. At the time of filing of this patent, the most common include 1) a wire connecting the coil system directly to the moving attachment of the MRI (General Electric implementation), 2) a wire connecting the coil system to the stationary part of the MRI (Philips implementation). 3) wire connecting the coil system to the MRI through connections provided in the patient support (Siemens implementation). Each of these means require the user to effect the connection of the coil system to the MRI by manually connecting a plug. Additional means could include electrical attachments that enable the wires to directly connect to the MRI without the operator needed to attach them. The process of setting the tabletop coil system on the patient support, or docking the patient support and stretcher to the magnet would perform the direct electrical connection to the MRI system. Electrical connection of the coil would be effected by the act of docking, or attachment of the stretcher, or tabletop coil to the apparatus. This may also include positioning the coil plug very close, but not completely in contact with the MRI connector. The user would then be required to perform the connection; however the benefit of positioning the connector close to the MRI connection would be to reduce the complexity of the setup process. This will become increasingly important when the number of required connections to the MRI (number of channels) increases.

Figure 1B:
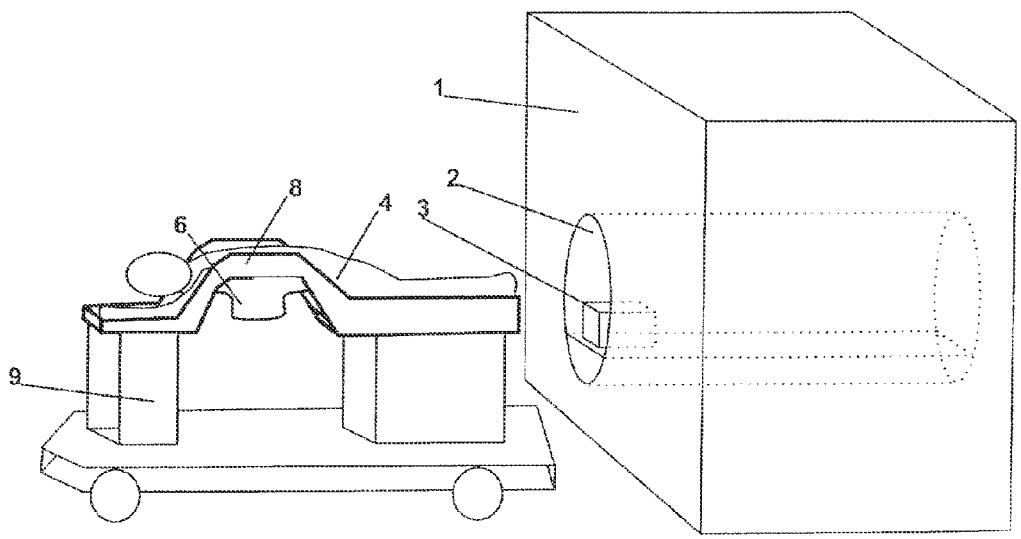
Figure 1C:
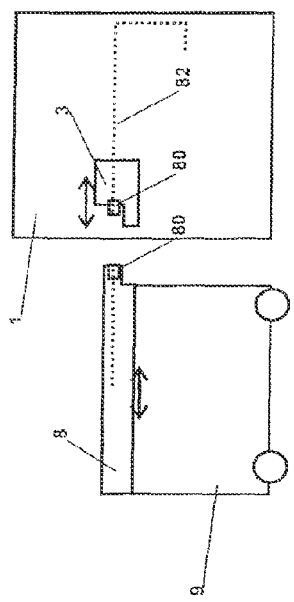
Figure 1E:
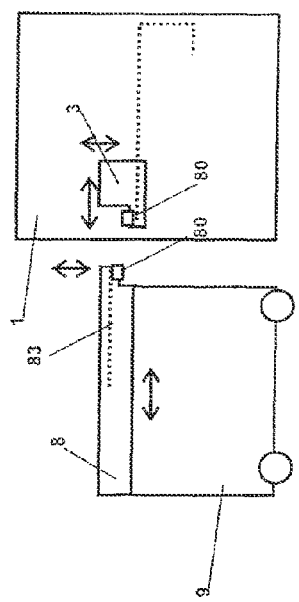

Various methods for connecting the RF cables (83) from the tabletop (8) to the MRI (1) are presented in FIG. 1C, D, E, F, G, H. The tabletop contains a set of cables to be connected to the MRI. These cables may be connected to the MRI through a moving station (3) that advances to mechanically and/or electrically connect the tabletop to the MRI. Electrical connectivity ensures the coils in the tabletop are connected to the MRI RF acquisition system. Mechanical connectivity ensures the tabletop can be transported into and out of the magnet without damaging the electrical components.

Figure 1G:
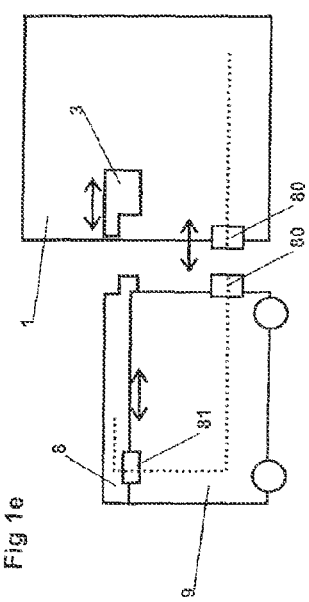
Figure 1D:
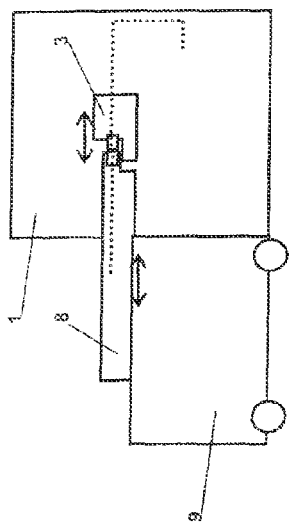
Figure 1F:
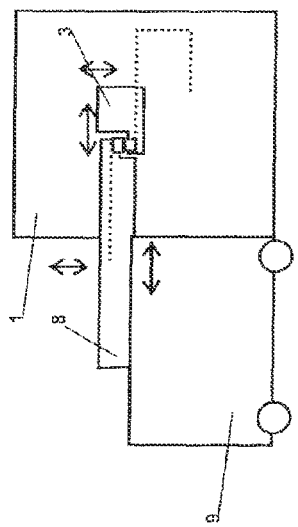
Figure 1H:
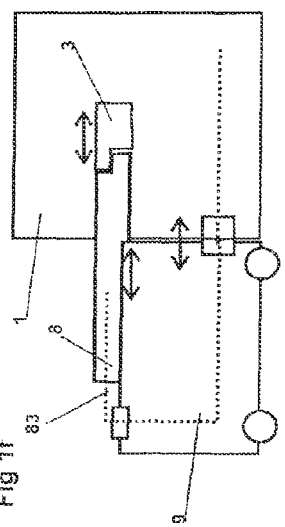

For magnets providing upwards of 16 data acquisition channels, it is highly desirable to provide a means to facilitate RF cable connection of the RF coils to the magnet. One such means would involve the specialized tabletop (tabletop designed for a specific, rather than general anatomic imaging function) to be attached to the magnet by way of a row of vertically or horizontally disposed RF connections with associated mechanical alignment. In the preferred embodiment the RF cables from the coils within the tabletop would terminate at the horizontal face of the tabletop at the end proximal to the MRI. In another embodiment, the RF cables would terminate in a way that they are directed in vertical face either directed upwards or downwards. FIG. 1C demonstrates the tabletop and stretcher in the undocked position. FIG. 1D demonstrates the table advanced into the magnet such that the tabletop (8) has been connected to the moving station (3) that supports a connection point (80) to the MRI RF system that corresponds to a connection point on the tabletop (80). FIG. 1F demonstrates the tabletop with vertical connectors undocked from the magnet. FIG. 1F demonstrates the tabletop attached after the tabletop has either been lowered on the moving station, or the moving station has been raised to meet the tabletop. FIG. 1G shows an alternative arrangement where the RF cables have been routed from the tabletop through the stretcher and from the stretcher into the magnet through connection points on the stretcher and magnet respectively (80). In this alternative arrangement the electrical connection of the tabletop to the MRI RF acquisition system is performed during the action docking the stretcher to the magnet.

Connection of the RF electronics of the tabletop to the magnet either through the moving station (3) or through a connection on the stretcher to the MRI would involve i) mechanical alignment and attachment of the stretcher to the magnet through a mechanical docking sequence, ii) the tabletop advancing to connect to the moving station (3), or the moving station advancing to connect to the tabletop. Connection of the tabletop to the moving station would be done by first providing a means to mechanically align the two mating connections by way of pins and holes, tapered alignment features or the like, such that the connections are mechanically aligned before the electrical connection is established. This is an essential feature for an automatic connection to the MRI. In one embodiment, these connectors would be coaxial connectors in which the center pin is shielded by an outer connector. In another embodiment the signal would be transmitted through inductively coupled connections. In a third embodiment the signal could be transmitted through optic fibers. The requirements for a mechanical alignment means would be maintained for all connection strategies.

The automatic connection of the table to the MRI through these electrical connections (80) through the moving station (3) or the stretcher is a novel concept having the benefits of reduced user interaction and provides a means to support a dense array of electrical connections (i.e. greater than 36 channels). Overcoming the electrical connector insertion force is significant when utilizing greater than 36 channels. In the proposed invention, mechanisms such as levers, cams, motorized linear or rotary actuators, or the like provides the required mechanical force required to facilitate connectivity to the magnet. Another aspect of the invention includes the addition of a cover that would protect the connectors from dirt, fluids, or patient/user contact. This cover would be lifted to protect the connectors automatically as the two sides approach each other. (For horizontal alignment, the cover would lift to cover the top of the connection area. For vertical alignment, the cover would lift to cover the side of the connection area). This cover would provide a mechanical barrier as well as a static charge barrier to protect associated circuitry.

Additional coil connection means could also include attachment to a wireless device which transmits to the MRI. All of the inventions presented in this patent document can be applied to all the various means of attaching the RF coil system to the MRI system. Additionally, an automatic coil tuning circuitry system may be provided in the tabletop. This circuitry must be positioned between the coils on the tabletop and the connection to the MRI. Currently, no stretcher system provides an integrated automatic coil tuning system and as such is a novel invention.

In the Prior Art, these types of tabletop systems do not provide modular support structures, anatomical immobilization devices, interventional access ports, means of device guidance, or means of attachment of additional RF structures. These systems are typically designed for a particular generalized anatomy and offer little to no flexibility with respect to positioning and imaging according to different clinical needs or body sizes.

A dedicated stretcher and tabletop system for breast imaging has been presented in the Prior Art (Piron et al, 200510080333). This system provides a unique patient support tabletop designed specifically for breast imaging and intervention. This system is presented in FIG. 1b. The stretcher provides a large access volume underneath the breasts, giving the physician improved access to the breasts for imaging preparation and interventional applications. In the Prior Art (Piron et al, 200510080333) a description of a coil system is presented in which the coils are not integral to the patient support and can be detached. This concept can be expanded upon greatly to fully take advantage of the open architecture of the system and the separation of the patient immobilization and RF coil system functions.

Through the use of additional support structures, patient-specific geometries and positioning can be accommodated in both a tabletop mounted, or dedicated stretcher-based coil system. The improved access that can be provided to the anatomy of interest through a dedicated stretcher-based system is shown in FIG. 1B. By providing removable sections of the structure, there are more directions from which the anatomy, in this case the breast, can be accessed. Additional support structures can be used to obtain optimized positioning of patient anatomies.

As an example, a patient support structure and RF system for imaging a patient in a prone position is shown in FIG. 2A. The main support structure (8) is similar for both the dedicated tabletop system and the stand-alone tabletop system. The figure shows how the two alternatives—placing a coil on top of the general purpose tabletop, versus replacing the general purpose stretcher and tabletop with a specialized, stretcher dedicated for a specialized tabletop which integrates or receives coil elements. The figures represent both the add-on tabletop version and the dedicated stretcher-based system similarly, though the tabletop add-on differs from the specialized tabletop in the length of the structure, where the dedicated stretcher/tabletop comprises a longer support for the entire length of the patient. The patient support structure (whether dedicated tabletop, or standalone) provides 1) structural support to position the patient in a comfortable position, 2) electrical cabling (11), 3) connectors and circuitry to enable connection/communication to the MRI system, 4) connections for secondary structural supports (14), 5) apertures to provide access room and to facilitate connection of substructures (9), 6) connection points (electrical and mechanical) to attach compression systems and immobilization devices. 7) Electrical connection of compression and immobilization devices. Coil elements can be integrated into the body of the structure as is currently done, or may be attached in a separable manner to the main support structure as claimed in this invention. According to the present invention, separable coils have electrical and/or magnetic connections, as well as mechanical connection to the main support structure. All signaling between the MRI and the coils takes place through the cables by way of the MRI connector (12). In the advent of wireless technology the signals would be transmitted via a similar wireless means.

A secondary support structure (15,16, 17) can be attached to the primary support structure (8) in order to optimally position the patient's tissues for imaging or interventional applications. These support structures hold a significant portion of the patient's weight and are integral to supporting the patient in a particular position. These structural elements are presented in FIG. 2B, C, D. In FIG. 2B a sternum support (15) is shown attached to the support structure. This is the preferred configuration for bilateral imaging of the breast. This sternum support may house an RF coil and may be electronically attached (14) to the cables (11) of the system. In FIG. 2C a unilateral breast support (16) is demonstrated to position the unimaged breast out of the way. In FIG. 2D a bilateral breast support (17) is inserted into the support structure. This support provides two volumes in which the breasts can rest and are substantially immobilized without significant compression. It is preferable to provide multiple support sizes for various breast sizes. These supports would be provided in varying dimensions according to breast anatomy sizing. In the extreme case, supports would provide a small cup, or plate, which could be used to image mastectomy patient, or the male breast. Combinations of different coils for different breast sizes may be used with this configuration.

This structure (17) may house RF coils for imaging of the breast and apertures though which the breast may be accessed. As with the sternum support which integrates coil elements, electrical connections or the like must be provided to transmit or receive signals to the MRI. Secondary support structures may house additional RF coils. Additionally, the bilateral support (17) may house a gradient coil, a transmit, receive or transceive coil. The ability to accept modular coil elements in an interchangeable support structure is a unique aspect of the present invention. Additionally, these secondary supports may provide specialized coils that facilitate specialized breast imaging, such as imaging or intervention of the axillary tail of the breast. This embodiment would include a lateral member that can be attached to the top of the compression frame on the inferior and superior portion of the compression, or patient support.

For instance, a separable sternum support can be used to hold an array of RF coils, and also support the weight, or maintain the patient in a fixed position. This support can be separated from the main body of the system, while still being able to be positioned fixedly for imaging.

In another embodiment, a secondary plate can be positioned externally (from sides or below the breast). These would be positioned in fixed positions relative to the anatomy. In a further embodiment a set of coils may compress the breast against the chest wall. In this configuration the coils may be used preferably to image mastectomy patients.

Additionally, this separable arrangement of coils provides a means in which additional coils may be provided at other locations on the structure. Considering the exemplary case of breast imaging, it may be advantageous to provide an array of coils additional to the coils used near the breast, to cover other regions of the body associated with breast cancer imaging. In current practice, a set of coils that are none-specific to breast cancer metastasis such as a body coil to scan various regions of the body. In the proposed invention, additional coils located in the primary support structure at locations such as near the liver, lobes of the lung, lymph nodes (neck, chest regions not covered by the breast coils, body, groin,) adrenal glands and brain as a non-limited set of examples. These coils would either be attached to the table for a specific patient, or would be selected during the scanning procedure for specific imaging sequences. In either case, this has not been presented in the prior-art for a specialized coil geometry. In one application these coils may only be selected for patients with a known cancer, while for the screening application, all available channels are used for coils positioned near the breast region as no-known cancer exists in these other regions.

Adjustable compression systems, anatomy support, positioning and immobilization devices are integrated in a separable manner to the patient support structure (FIG. 3). They also provide a basis for positioning and guiding imaging or interventional devices to an anatomy of interest. These compression systems (18, 19) may consist of flat plates as shown being introduced to the system in FIG. 3A, or members having surfaces that conform to the anatomy or to a desired shape. These compression systems are movably and lockably disposed on tracks, rail guides, or held by mechanical arms or the like. Where multiple degrees of freedom are desired for plate adjustment, lockable joints such as gimbals having several degrees of freedom may be used, or a second guide rail may be mounted on top of a first (and a third on top of a second), permitting adjustment in multiple independent axes. A combination of mechanisms may be used to provide both linear and rotational adjustment. These positioning devices are locked in place using clamps, mating threads, straps, friction fits, or other immobilization means. It is also possible to deliver or to maintain a patient supporting, immobilizing, or compressive force by coupling a mechanical, electrical, hydraulic or pneumatic actuator to the member. Through the use of an open architecture system, whether an add-on tabletop system such as shown in FIG. 1A or in a dedicated stretcher-based system as presented in FIG. 1B, the anatomy can be supported, immobilized, compressed or repositioned in various directions while the patient remains immobile, lying on the support structure. This is currently only possible in a limited manner in the prior art by tabletop add-on breast imaging systems providing medial and lateral compression in a left-right direction. One system in the Prior Art provides access to the breast from the anterior direction (Piron et al., described above). Shown in FIG. 3B is a compression plate approaching from the lateral direction (19) and a compression plate approaching from the anterior direction (18). Structures can be delivered from a medial approach in a similar way. This open architecture permits removing and attaching compression plates and coils from various directions without removing the patient from the apparatus. Structures other than compression plates also may be introduced into the volume (9), these are referred to as secondary infrastructure devices. FIG. 3C shows an anterior structural plate (20) that hinges in the sagittal plane, shown here hinged about the thorax region of the patient, and a lateral structural plate (21) that hinges in a coronal plane, shown hinged about the thorax region of the patient. These plates may pivot or slide into the volume of interest, or may be completely detached and reattached as required. These plates may be delivered and locked in place relative to the main support structure by various mechanical clamping or fixation means (22).

These structures are brought into the structure's open access volume for purposes of 1) protecting anatomy from rubbing against the MRI's bore as the patient is advanced to the imaging position, 2) providing attachment points and fixation means for other structures, imaging or interventional devices, 3) providing additional coil structure support and attachment points, 4) (when used with a special purpose tabletop having a dedicated stretcher) providing a structure and surface which may bear the tabletop's weight when advancing into the bore of the magnet, 5) for catching blood, or 6) for any combination of these purposes. It may also be preferable to communicate the locked or unlocked conditions of these plates through mechanical locking mechanisms, electrical signals or any other communication means to indicate to the magnet or the user if the plates are not in the proper position for imaging or for advancing to the imaging position. This provides a means to ensure the patient will not be advanced into the magnet until all plates are positioned appropriately.

Figure 3A:
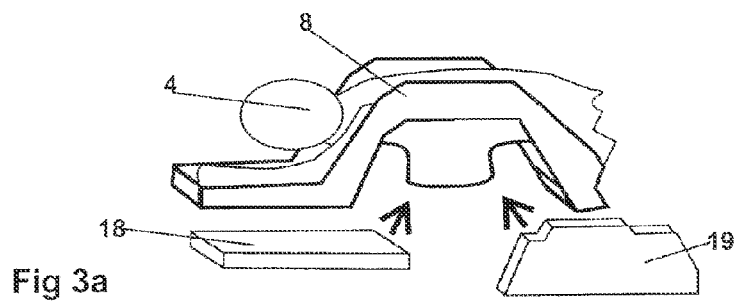
FIG. 3—Shows the front section of patient support structure with the patient in position with various compression plates and secondary infrastructure attachments. A. Shows an anterior plate and lateral plate being attached to the main structure with the patient in position. B. Shows the anterior plate and lateral plate in position. C. Shows an anterior and lateral plate introduced as a secondary structure pivoting from an attachment on the main apparatus. D. Shows an anterior coil plate and a lateral coil plate being introduced on the main support structure. E. Shows the anterior and lateral coil plates in place.
Figure 3B:
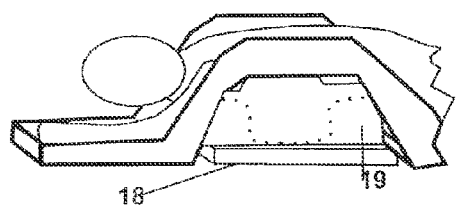
Figure 3C:
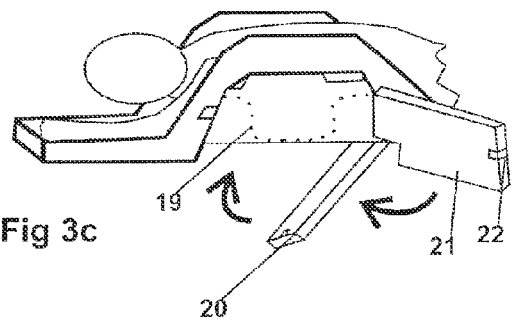
Figure 3D:
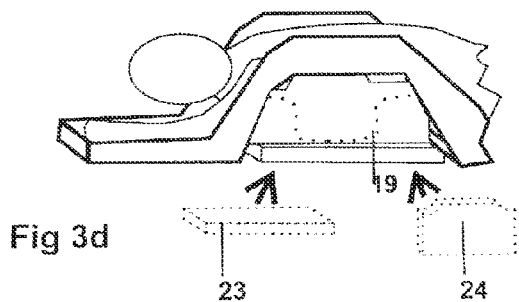
Figure 3E:
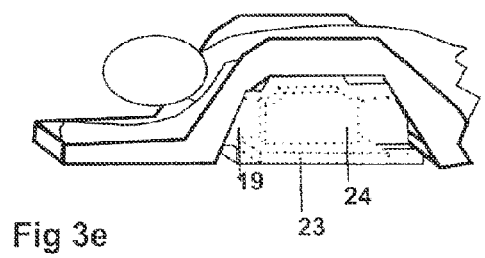

The compression plates (18, 19) additionally provide mountings to which removable RF coil systems (23, 24), as shown being introduced to the system in FIGS. 3D and 3E, or magnetic field gradient producing coils, or "gradient" coils may be attached. These mountings may provide both mechanical connections to the compression system and, simultaneously signal connectivity to the MRI imaging system, such that the act of connecting the coil element or elements to the movable compression plate also connects that coil's signals to the MRI. One benefit of an RF coil system that is separable from the main support, the secondary support structures and the compression/immobilization system is that the patient may remain in the identical position while various RF coil systems can be attached and removed. This is a unique and fundamental concept.

Decoupling the anatomical positioning and immobilization from the delivery of coil elements and other devices permits modular attachment of devices according to the application while the patient remains in an unchanged conformation. Additionally RF coil systems may be attached to or built directly into the compression frames. These compression frames would then be connected to the main support structure both mechanically and electrically through a single locking/fixation means. There would be no need to attach a moveable coil to the MRI with a separate cable or other signal coupling means if the signal path is completed through the fixation or locking means. This may be accomplished by (for example) providing sliding electrical contacts along the adjustment range of the compression plate's fixation means. This connection could either be constantly in contact, or it could be closed by the act of fixing the coils in place with a suitable fixation means such as a clamp, cam lock, friction fit, or the like.

The use of modular magnetic field gradient producing electronics, as described is unique and applicable to the full range of organs, body regions and limbs (in addition to the breasts) identified above. As gradient coils are primarily part of the MR imaging system, the departure of integrating these into the patient support bed is unique. These gradient coils, connection of these gradient coils to the MRI by signal producing cables and wires, and mechanical means of affixing the coils in a modular manner to the patient support structure or its compression plates are novel aspects of the technology. Furthermore, the attachment of the coils to the support structure, and then to the MRI system by wireless technology (e.g., RF, optical transmission), and the like is novel. Furthermore, the ability of completing and RF circuit or imaging coil loop upon locking of the compression plates such that the coil is active in the locked position, and in-active in the unlocked position is novel and provides the benefit of ensuring the plates will not move during imaging.

Further, the method of attachment of the coil to the compression plate can be configured to automatically select appropriate signal channels and terminate unused channels directly through the connector. A plug, referred to herein as a termination plug, provides electrical terminations for the end of a set of signaling cables or lines. Using a suitable plug configuration of various electrical components such as electrical shorts, opens or various loading (impedance from resistors, inductors or capacitors), along with appropriately mechanically arranged keyed coil plates, enables determination and routing of the channels to the MRI to happen automatically, with no need for multiplexing circuitry. To accomplish this, each coil plate mates with the cabling system through an N terminal plug, where N is the maximum number of coils that can be included within each coil plate. For plates with fewer than N coils, a subset of those plugs connect to the coils, with the remaining plugs connected to line termination circuitry within the coil plate. These N lines from each coil plate must be combined down to the number of input channels of the MR system. By properly configuring the connector geometry, each unused, terminated connection line of a coil plate can be wired in parallel with an active coil on a different connector, thus providing connection to a full set of active MR channels automatically. Unused lengths parts of the cable system are terminated when coils are plugged in to it. The mere fact of attachment of coils and coil arrays through terminating plugs is novel. Also, a coil plate is proposed which has a connector which will reverse the polarity of its connection when it is physically connected in the opposite orientation. Further, a coil plate may have a connector plug which may mate with a connector receptacle in a variety of different orientations (e.g., 0 degrees, 90 degrees, 180 degrees, intermediate degrees, etc), wherein the orientation of its connection determines which channels of the cable system (and therefore MRI) the coil plate connects with (and which cables are terminated).

The compression/immobilization system should preferably consist of materials giving rise to minimal artifacts when imaging using other imaging modalities such as ultrasound, X-ray. PET, CT, optical, etc. This can be accomplished through appropriate matching of materials such that the excitation or detection of signals are minimally affected by the existence of the compression/immobilization system (i.e. acoustically transparent windows, optically transparent windows, optically translucent materials, radiolucent materials, non-magnetic materials etc).

Radiofrequency Antennas

Figure 4A:
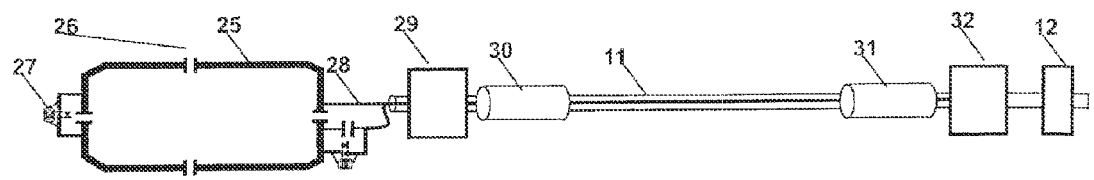
FIG. 4—A. Shows a single loop coil with the associated circuitry. B. Shows an array of single loop coils with a multiplexing device. C. Shows two loop coils with an electrical connector enabling the coil to be removed from the cable. D. Shows a small loop coil. E. Shows a large loop coil. F. Shows a butterfly coil with two lobes and three lobes. G. Shows a transmission line coil. H. Shows a looped transmission line coil.

The antennae, or RF coils (which are also called simply "coils") used with such an apparatus include transmit and receive coils of various designs. A typical RF coil design for a simple receive-only loop coil is presented in FIG. 4A. This RF antenna (33) consists of basic RF components including the RF coil conductor (25), broken into multiple segments with distributed capacitors (26). At one of the junctions is a passive blocking circuit (27), with an additional active blocking circuit (28) which is activated by a bias signal from the MRI. Various additional circuits and components are desirable and will be considered to be included when appropriate when referring to all RF implementations throughout this document. Preamplifiers and conditioning circuitry (29, 32) may be included either close to the coil as is preferred for optimal SNR, or further towards the MRI connector (12). The pre-amplifiers can be included either 1) on the MRI system, 2) on the support structure, or 3) on the coil. There are benefits to positioning the preamplifiers on the coils, as they can be easily replaced, can be optimized for particular applications and can provide greater SNR improvement the closer they are to the coil. Additionally, current shield chokes or baluns (30, 31) or other like components may be placed on the cable, on the coil, or anywhere throughout the RF system to provide appropriate current chokes which minimize electrical currents in the shield of the RF conductors. These concepts have been presented in the Prior Art, and is presented here as background material.

Figure 4B:
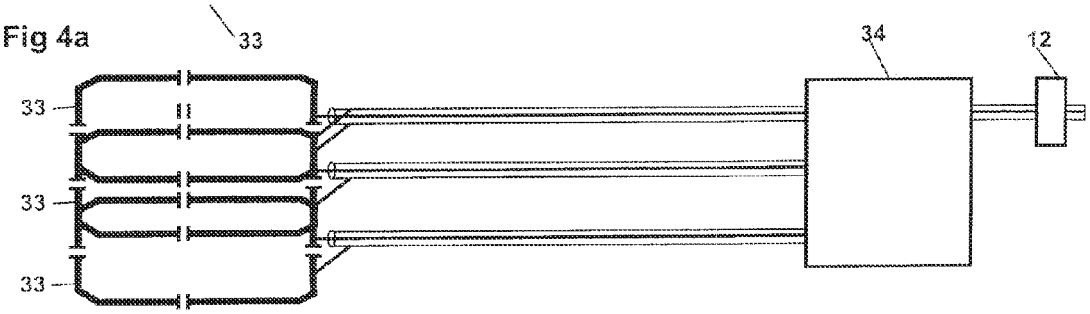
Figure 4C:
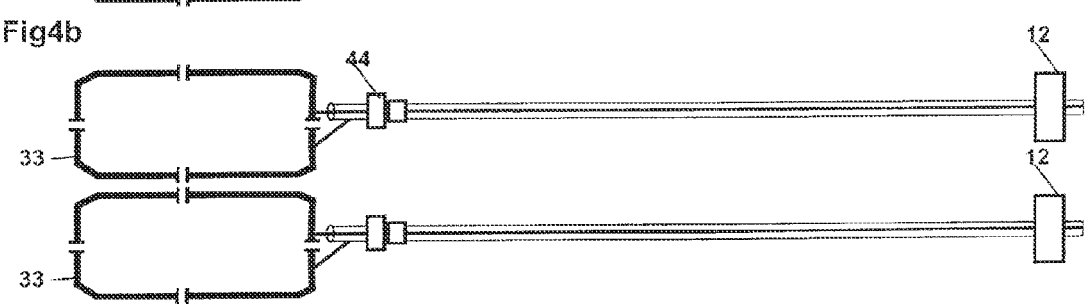

When more than one coil is provided in the system there are many ways in which they can be selected. In FIG. 4B, three coils are shown, decoupled from one another by an appropriate overlap which brings mutual inductance to zero. In order to select one coil, a multiplexer (34) can be used. This is a common way of selecting which coils are receiving or transmitting signals to the MRI when a subset of the full available set is required. This is well known in the prior art. In FIG. 4C. two coils are shown with an electrical connector (44) in the cable (11). When the coils are detached from the cable, signals to or from the MRI can not be transferred. In this way various coils can be removed and interchanged as is appropriate. The preferred electrical embodiment employs coaxial connectors; however various connectors can be used. Further, when a coil is detached from a cable, circuitry can be enabled, either mechanically through the act of detachment or electronically, which provides an appropriate signal or electrical characteristic on the cable to disable or detach that cable's connection to the MRI, or remove any effect that cable may have on the imaging system.

Figures 4D, 4E, 4F, 4G, 4H:
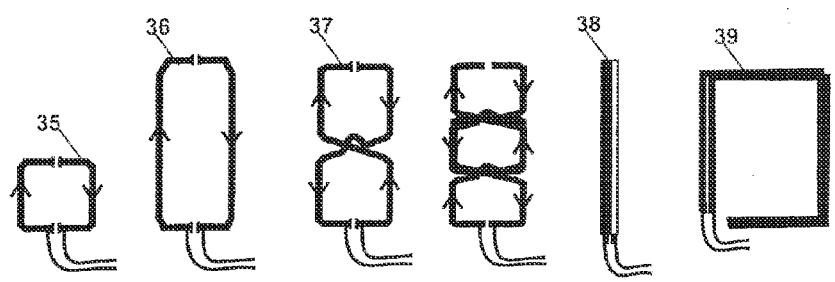

In reference to FIG. 4, Small (35) or large (36) loop antennas, as shown in FIG. 4D and 4E, respectively, provide high SNR and can be sized appropriately to the anatomy. Butterfly coils (37) can be combined with loop coils to form a quadrature configuration, as shown in FIG. 4F. This has been presented in the Prior art. Multilobe butterfly coils have not been extensively used in multiple coil geometries however. Microstrip Transmission line coils (38) (Zhang 2002/0079996), as shown in FIG. 4D, can be utilized in densely packed configurations in a variety of geometries. These antennas can be combined with loop and/or butterfly coils in densely packed arrangements while still providing substantially orthogonal fields that lead to high SNR and unique fields that can lead to high accelerations for parallel imaging. These microstrip coils can be fixed into loop, or hybrid structures to form that appropriate imaging sensitivity profile (39), as shown in FIG. 4H. Additionally opposed solenoid RF antennas can provide good local imaging with the benefit of minimal coupling with surrounding coils.

A fundamental element to the invention presented herein is the ability to decouple a large number of coils in a confined space by use of combinations of coils which are intrinsically decoupled from one another. As a set, a combination of loop coil and butterfly coil may be positioned in such a way that they can be placed co-planar to one another and not be coupled. In this way a loop and a butterfly coil exceeding at least 3 cm in its longest dimension, can be positioned in a location crosswise from a loop coil, in a clinically useful geometry and not diminish imaging quality through significant coupling effects. In this way coil geometries can be used that are conducive with a separable RF system design as presented (i.e. coils located close to the anatomy, such as a coil 5 mm from the volume of interest, located on more than one side of the volume simultaneously). Additionally combinations of butterfly coils, or three or more lobed geometries (i.e., loop coils with more than one self crossing point), can be used in such an arrangement where the decoupling is minimized. Some of these preferred geometries, where butterfly coils are used with loop coils are presented in FIG. 8.

Combining these coils in appropriate arrangements within this modular system provides various opportunities for optimizing imaging for various applications.

RF Coil Housing

Figure 5H:
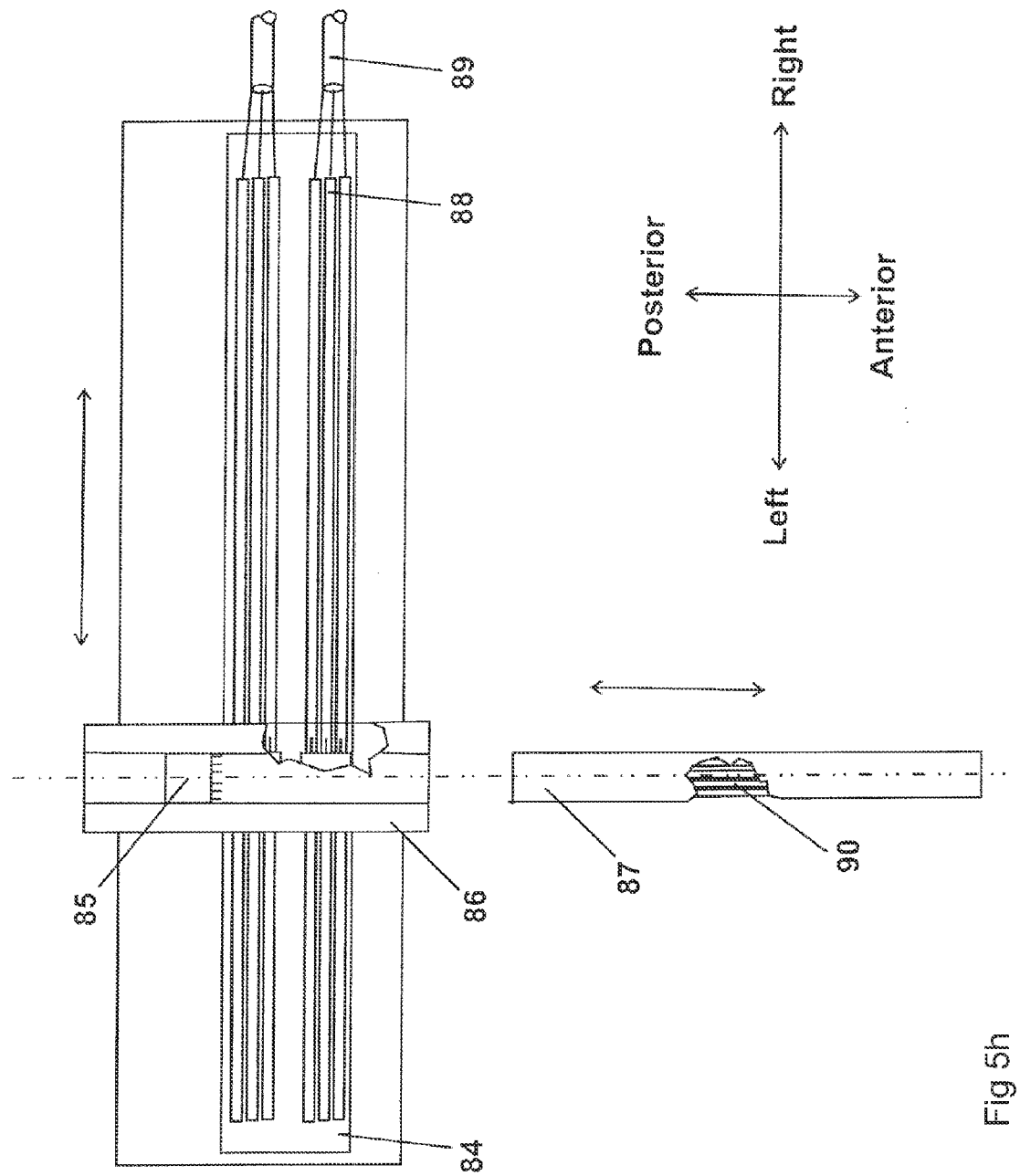
FIG. 5—A. Shows a loop coil contained in a coil housing with a coaxial wire for connection. B. Shows a loop coil contained in a coil housing with an electrical/mechanical connector. C. Shows a loop coil with an RF to optical conversion circuit and a mechanical/optical connection. D. Shows a side view of a breast support structure with a patient on top. The compression plate has an aperture in which a coil plate is attached. E. Shows a coil plate attached to the compression frame with a cable connection to the MRI. F. Shows a coil plate attached to the compression frame with an electrical/mechanical connection to the compression plate. G. Shows a coil plate attached to the compression frame with a wireless connection to the compression frame. The compression frame is itself wirelessly or electrically connected to the MRI. H. Shows a side view of rail (top) that supports a compression frame slider (middle) and a coil (bottom) as an additional wireless implementation.

The RF coils must be embedded in a housing (40) that protects the electronics from damage, and protects the patient from potential burns or heating. The coil housing may also provide an RF shield which can be integrated into the housing. Examples of such coil housings are shown in FIG. 5A. Here the coil (33) consists of a coil housing (40), with the electronics embedded within the coil housing. In this presented configuration an aperture (41) in the middle of the coil housing provides an access port in which interventional procedures may be performed. In order to connect the coil electronics to the MRI electronics, a cable (11) runs out of the coil housing as is common with most coils. Alternatively, in lieu of a cable on the coil, a direct electrical/mechanical connection (42) can be made from the coil to cabling running to the MRI through various potential attachment points on the structure or on the compression plates as shown in FIG. 5B. Alternatively, an optical signal may be used to transmit the received imaging information from the coil to the MRI. This is demonstrated in FIG. 5C where an electrical/optical signal conversion takes place on the coil plate or in a structure which is connected to the coil plate and the optical signal is transmitted to the MRI via fiber optic cables or optical signals transmitted through the air. This conversion can take place inside an imaging tabletop or in a structure connected to the imaging tabletop. In connection with the optical transmission of imaging data, the MRI is fitted with a means of decoding or demodulating such data in order to process it in the ordinary way. Each of the coil housings presented must provide the following features: 1) Mechanical attachment mechanisms, 2) Means of coupling signal to the MRI, 3) Physical housing to protect electronics and patient which is impervious to fluids and may be appropriately cleaned and/or disinfected.

According to the present invention, coil housings or tabletops may also contain batteries or capacitors which would be used to operate coils that are wirelessly integrated into the RF system (e.g. using telemetry or an optical connection). If these coils are receive-only coils, a DC voltage is required to provide a blocking voltage to the coil during transmit imaging mode, or power may be required to activate amplifiers located in the electronics. The coil housing may include a means of connecting to a battery recharging station. This may be provided by way of an electrical connection to the coil housing from the recharging station, through the housing to a rechargeable battery internal to the housing. This battery may then be electrically attached to the coil circuitry where it can power connected amplifiers, or activate diodes to perform switching circuitry. Alternately, the coil may be powered by a fuel cell, which fuel cell may be recharged while in the coil housing, or which may be removed for purposes of replacement and/or recharging.

Coils having cryogenic cooling may be refilled with cryogen using this same battery charging station, or a separate charging station. A coil housing may contain or integrate a cryogen containment device that contains cryogen coolant (e.g. liquid Helium, liquid Nitrogen) so as to reduce the electrical noise arising from the electronics and the coil conductor. The cryogen levels in the coil would need to be recharged, or refilled over time due to the gradual loss of cryogenic coolant from the containing housing. A separable coil with such a cryogen container would benefit from a recharging station which refills the coil with cryogen (either on demand, automatically, or otherwise). This charging station consists of a cryogen containment volume and a means to supply this to the coil housing. When the coil is attached to this charging unit, it is filled with cryogen through an opening and a sealable valve contained in the coil housing. An additional novel concept would be to combine the battery charging and cryogen refilling functions into a single station. As such the battery levels used to charge the active components of the coil, and the cryogen levels used to cool the coil, can be refreshed in a single step. Additionally, such a coil having cryogenic coolant can use the Seebeck voltage effect to generate a small amount of electrical power. This power can be used directly to provide coil blocking or to power the transmission of signals from the coil, or the power can be used to charge a battery which is in turn used to do these things.

Coil Attachment Point Positions

RF coils may be integrated into the coil system through any combination of a variety of means: 1) Embedded (non separable) coils in the support structure, 2) Embedded coils in non-separable, but movable structures, 3) Separable RF coils in coil housings attached to the compression frames, 4) Separable RF coils in coil housings attached directly to the support structure, 5) Separable secondary support structures containing RF coils. As presented in FIG. 2, embedded coils in case 1) and 2) can be directly connected to the MRI connector (12) by way of the traditional means of electrical connection. Separable coils 3), 4), 5) may be connected to the MRI via a connection panel (13) or port (14) provided within the support structure (8) which is then attached to the MRI connection (12) by way of electrical cables (11) (or other such means). RF coils that are attached to the moveable elements of the system such as the compression plates, the secondary infrastructure or embedded within the compression plates have the advantage of being placed very close to the anatomy resulting in high signal acquisition.

Connection points are provided in the support structure at points that are accessible to the MRI technologist and located at various positions on the main support as indicated in FIGS. 5D, 5E, 5F, and FIG. 2. These connections would consist of single or multiple individual electrical, optical or inductive connections housed within a mechanical support structure. In cases of arrays of densely packed RF coils, these connectors would consist of many independent connectors. RF coils may be attached to the connection panel or ports by way of multiple means including:

1) Electrical cable with terminating connector attached directly to connection panel. (preferably a coaxial or similarly shielded connector)

2) Direct electrical connection provided through an electrical/mechanical connection housed in the coil form.

3) Magnetically inductive (wireless) connection from coil to the connector panel.

4) Optical connection (with or without fibre-optic cable) from the coil to the connector panel.

These connection points should provide mechanical integrity and in cases where the coils may be exposed to fluids or bio-contamination, must be impervious to these fluids and be easily cleaned and disinfected. Additionally these connection points should provide unique physical connections so that only certain coils can be connected to certain connection ports as appropriate.

One exemplary implementation includes a number of sets of electrical conductors (88) disposed along two sets of sliding rails. The number of sets of electrical conductors is equal to the number of channels of the MRI system. This invention is presented in FIG. 5H. Here a rail (84) supports a mechanical slider (86). Along this rail are multiple sets of multiple parallel conductors (88) in which each set terminates on a coaxial cable (89). In the exemplary case, there are two sets each having three parallel conductors. In the exemplary embodiment, each channel is represented by a set of three conductors, one centre conductor for the central conductor of the coaxial wire, another two used for the outer conductor of the coaxial conductor. The relative position and thickness of three conductors relative to each other enable matching of the conductor to enable impedance matching for the electrical system. In a similar embodiment, multiple sets of two conductors are used, connected in alternation with inner and outer conductors of the coaxial cable. This alternation, whether among sets of three or sets of two conductors is necessary to provide a substantial degree of shielding between adjacent channels of the MRI signals.

The slider (86) is fitted with brushes or spring contacts which connect electrically to the sets of parallel conductors either continuously, or only when the slider (86) is locked in place.

The coil and coil frame (87) supports similar sets of parallel conductors (90) disposed along a different direction of adjustability of the coil frame. These conductors are positioned externally to the coil enclosure and connect to the coils housed within the enclosure. These conductors are aligned with a mating set of conductors contained within a T slot in the mechanical slider (86). When the conductors on this slider are locked into place with the coil enclosure by way of a locking mechanism, the two sets of conductors are in electrical contact.

Such an arrangement provides a means of locking the slider and/or coil mechanically and completing the electrical connectivity between the coils (87) and the cables (89) in one action. Regardless of adjusting the positions of the coil frame in the slider and the slider in the rail, there are multiple electrical connection from the coil contained in the housing to the wires that are connected to the MRI. Although the presented implementation uses T slots and a set of three conductors, various other mechanical and electrical configurations may be used that do not deviate from the spirit of this invention, that spirit being the ability to connect a set of cables at continuously variable positions through mechanical positioning mechanisms. This ensures no cables interfere while positioning coil plates, and electrical continuity checking can determine if all plates in the system have been locked into position.

Coil Selection and Switching

Bilateral imaging applications such as breast imaging when using arrays of multiple coils can make use of a means of selecting subsets of coils to collect only MR signals from the volume of interest. In the case of bilateral contrast-enhanced breast imaging, it is desired to obtain individual breast volumes independently. Therefore a means of selecting a subset of coils during image acquisition of one breast, and another subset of coils for another breast is preferable. This is also required for imaging applications when selecting to image or excite sub-volumes of interest and additionally in applications where sets of transmit coils that only comprise a subset of the full number of RF coils may be desired to be activated.

Methods of selecting or deactivating coils include selecting coils by electrical activation or deactivation, mechanical modification of the coil such that the coil circuit is modified, opened or closed or the removal and reconnection of coils. One means of switching coils for different imaging configurations pertains to the physical separation of the coil from the system, in particular the removal of the coil and coil housing from the connection to the MRI. If another coil or coil array is not put in place of the removed coil, a termination circuit, an open circuit, an appropriate resistive load, such as a 50 Ohm load, a closed circuit, or a circuit designed to detune the coil may be connected in its place, either automatically or manually. This can be applied to coils that are connected to the system by electrical connection, electrical/mechanical connection, inductively coupled or optically coupled coils.

Another coil selection option includes electrical deactivation of the coil through a blocking signal (typically a bias voltage) to a detuning circuit. These coils may be selected so as to optimize the total number of coils which are imaging an appropriate volume. Electrical coil selection can be accomplished by 1) user selection of coil configuration files which program the MRI to send an appropriate blocking signal to the coils, 2) automated switching based on external signals generated through the MR control pulses., e.g. alternating activation and deactivation of coils in such a manner to decouple them appropriately or to maximize the number of active signals as is preferable with imaging of bilateral anatomy. 3) user selection through an external signal not provided through the MRI. This signal may be electrically, optically or inductively provided. 4) Automated selection of coils based on loading characteristics of the coils as reflected by the signal provided by the coil, 5) Analysis of the individual signals arriving at the MRI and their omission or inclusion in the reconstruction. 6) Programmed switching of coils using optical signals. These automated techniques require a signal to be measured (an impedance measurement from the coil, an MR signal measurement or an optical measurement) to determine whether each individual coil element is making a positive contribution to the overall field-of-view or SNR. This is a particularly important consideration for breast imaging where breast sizes vary significantly and where some subset of coils may not contribute signal to the image reconstruction and so should be disabled or disregarded. Rather than simply ignoring the input of one or more coils, it is sometimes advantageous to disconnect, deactivate or remove one or more coils. If one or more coils in an array is deactivated or disconnected or removed, it does not contribute electrical noise to the reconstructed image in the same way that an active, connected coil would. Additionally, it cannot provide unwanted coupling between other coils when thus negated. In one embodiment of the present invention, more coils are provided in proximity to the region of interest than can possibly be used simultaneously. Various means are used to select from among the available coil elements the most beneficial coil elements. The means of coil selection and schemes for coil deactivation are given above.

Switching, with external circuitry and multiplexing of channels, enables more coils to be used present in an array than the total number of available receive channels available on the MRI. For instance a 16 coil element breast coil array can be used with an 8 channel MRI. This concept has been proposed in the prior art, however this has not been considered for an expandable system as presented and did not anticipate the various embodiments presented in this application. This multiplexing capability can be provided in the dedicated stretcher-based or tabletop add-on coil as well as within the MRI electronics. Additionally, switching circuitry can be integrated to enable proper transmission of the receive coil signals, transmit signals and blocking signals for coil deactivation as has been presented in the prior art (U.S. Pat. No. 6,867,593 Menon et al). Integrating this switching technology into the stretcher has not been anticipated in the Prior Art and offers significant advantages.

Additionally, mechanical/electrical switches may be used to force the circuit to be inactive. This is primarily a mechanical decoupling where the coils may be left in place, with a switch either completing or breaking the circuit, or enabling an additional circuit which disengages or decouples the coil from the system. Furthermore, multiple coils may be arranged within a coil plate in a manner that enables certain coils when the coil plate is inserted in a specific orientation, leaving the other coils inactive. This could be a gravity switch, which selects and deactivates predetermined coils depending on in which orientation the plate is fixed. Alternatively, coils could be activated/deactivated by the orientation in which the coil frame's connector is introduced into the corresponding receptacle.

Coil Element Array Designs:

Combinations of loop coils, saddle coils, transmission line antennas, butterfly coils, dipoles, solenoid coils, opposed solenoid/self-inductive can be used in the present invention. These coils can be used as phased array or as quadrature or circularly polarized configurations. The preferred embodiments include arrangements where multiple coils are selected on the basis of being sized appropriately to the patient anatomy, with each coil imaging substantially independent sub-volumes of the total imaging volume. In this way the combined signal to noise ratio from all the coils can be maximized. In particular, the combination of a loop coil, a butterfly coil and in some arrangements a transmission line coil all three lying in the same plane or in nearby parallel planes will form fields whose field lines are, in most places, close to orthogonal to each other. Having substantially orthogonal field lines helps to reduce inductive coupling between coils. In this way coils can be densely packed to cover an imaging volume without interfering with one another, giving rise to optimal SNR.

Individual Coil Configurations

Signals from individual coil elements can be combined in phased-array, quadrature or circularly polarized arrangements. The preferred embodiments are presented with interchangeable coil plates containing coils in phased array and quadrature arrangements in various geometries and various orientations. The arrangement of the coils on these plates contributes to the overall sensitivity profile and field-of-view of the combined coil array. Therefore the size, position, phase variation and orientation of the coils must be considered to optimize the overall sensitivity, field uniformity, field coverage, coil coupling and parallel imaging characteristics of the entire coil arrangement. FIG. 6 shows a number of loop coils (36) arranged and permanently mounted together within a movable coil plate (40). For breast imaging, a set of four loop coils are presented with long axis in the Y direction (corresponding to patient Anterior/Posterior orientation) in FIG. 6A. This has not been presented in the Prior Art for breast imaging. The polarity of the field attributed to each coil is in the same direction. Decoupling of adjacent coils is performed by overlapping the coils slightly. In FIG. 6B, the direction (polarity) of the field is reversed in alternate coil. In this manner the coils flux or field generated by the combined coils can be more effectively decoupled in some arrangements. A similar coil array to FIG. 6A, is shown in FIG. 6C differing only in height where smaller coils are used (35). Here the aspect ratio is closer to 1:1 width to height, opposed to slender coils in FIG. 6B, where the ratio is 2:1 up to 5:1 in dense arrays. Placement of the coils (36) in the horizontal orientation as depicted in FIG. 6D demonstrates a four coil arrangement with the long axis of the coils aligned with the long axis of the coil plate. An arrangement of four butterfly coils (37) is presented in FIG. 6E. These coil plates can also be arranged with loop coils as shown in FIG. 6F, as they produce unique coil fields for better parallel imaging capability.

Loop and butterfly coils can be overlapped, as shown in FIG. 6G, such that their fields are orthogonal to one another. In this way a dense packing of 8 coils with unique imaging fields of view can be attained. These coils can be arranged with long axes aligned with the long axis of the coil plate as shown in FIG. 6H. Transmission line coils (38) can be arranged with their length along the main magnetic field of the magnet as shown in FIG. 6I. The lengths of these coils can be modified to fit the contour of a compressed breast. These concepts have not been presented in the Prior Art and are novel. Alternatively, transmission line coils can be used in a configuration where the line is shaped into the geometry of a loop coil, but which loop is not actually closed. Two such coils are presented in 6J. With the transmission line coils in an open loop geometry, the coil operates similarly to a single loop coil with the field directed in one direction. As a transmission line coil field tends to be directed in one direction, this geometry is beneficial when considering these coils can be used in an array where the coils are positioned with their ground planes directed towards each other.

Loop coils and transmission line coils can be combined to create dense arrays of coils as shown in FIG. 6K where 8 coils are presented. Further, butterfly, loop and transmission line coils can be arranged to create a twelve coil array as shown in FIG. 6L in which the fields are relatively independent. This arrangement of densely packed coils leads to arrangements of coils optimally sized to the anatomy of interest and providing for high acceleration factors with respect to parallel imaging capabilities.

Various phased array configurations have been used for cardiac coil systems in which two rows of coils are used in order to provide for parallel imaging (e.g., SENSE) accelerations in two directions along the coil plate. A breast coil combining many loop, butterfly and saddle coils has been presented, however this is in a fixed arrangement (Qu et al, US 2005/0104591 A1) where positions and types of individual coil elements cannot be modified. Additionally, coil systems have been presented in which individual coil elements are shown to be combined in linear arrangements (Vij, U.S. Pat. No. 6,498,489). However no attempt has been made to decouple the imaging and support functions of the coils and there has been no attempt made in which to decouple the sets of coils from one another. Additionally, none of the coil arrangements presented in FIG. 6 have been proposed in the context of imaging with the plates on opposing sides of the imaging volume.

The TIM® system developed by Siemens Medical combines multiple coil elements, some of which are embedded within the patient support table. The MRI system actively blocks and detunes some elements in the array of coils. This is a significantly different concept than proposed. Additionally, the TIM® system is a generalized RF system design in which the generalized tabletop has been developed to handle all potential imaging applications without specifically providing for optimized coil arrangements or positioning. Applications such as breast imaging require a dedicated support structure in which modular coil arrangements can be utilized.

Coil Array Configuration

The coil plates should preferably be arranged in a medial/lateral arrangement as demonstrated in an axial view of the coil arrangements shown in FIG. 7. FIG. 7A presents a unilateral breast imaging application where a single breast of interest is immobilized and compressed between two compression plates which can be adjusted in a left/right direction and locked in place, while the other breast is compressed against the chest wall by a contralateral breast support. In FIG. 7A) medial (47) and lateral (24) coil plates are supported by a pair of compression frames. The ability to move these coil plates close to the breast significantly improves coil reception. Implementations of such a coil configuration have been presented in the Prior Art, various geometries of these coils were not detailed (Piron et al, 2005/0080333). This application presents detailed coil arrangements that can be used with such a configuration, and additionally expands beyond this concept with coil arrays presented in various other arrangements and geometries that enable improved coil decoupling.

Figure 7D:
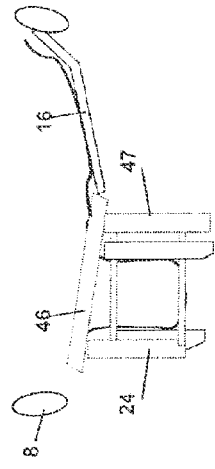
FIG. 7—Shows an axial view of a patient with breasts in different conformations. A. Shows the breast in a unilateral configuration with various coil plate arrangements. B. Shows a bilateral configuration with four independent medial/lateral plates. C. Shows a bilateral configuration with a combined posterior and medial plate structure. D. Shows a unilateral breast with attached coil array. E. Shows a bilateral configuration of D. F. Shows a bilateral arrangement without compression.
Figure 7E:
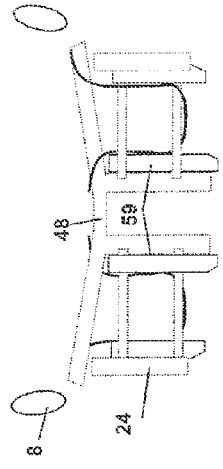
Figure 7F:
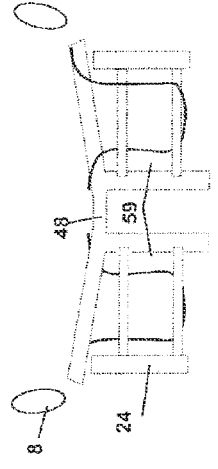
Figure 7A:
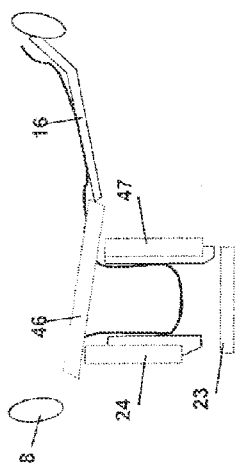
Figure 7B:
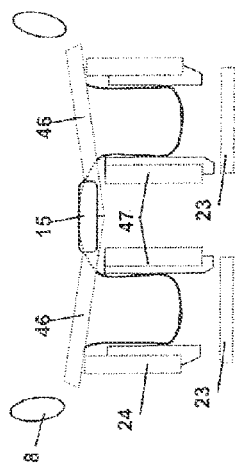

In FIG. 7B, a bilateral coil geometry is presented in which two lateral compression plates (24) contain coils and two medial compression plates contain coil plates (47). Additional anterior coil plates (23) can be attached to the compression frames or attached to the main support structure (8), as well as posterior coil plates, or coil structures (46) which are disposed against the chest wall, having large apertures which admit the breast. These coils may also be moved relative to the support structure. In the preferred embodiment the medial/lateral coils will primarily move left and right, while the anterior/posterior coils will primarily move up/down. It is also desirable to have a small adjustment range of the medial-lateral plates in the anterior-posterior direction (up to 30 cm for standard breast imaging), and to have a left-right adjustment range for the anterior-posterior coils (up to 50 cm for standard breast imaging). For bilateral imaging applications, four separate lateral-medial compression plates provide compression for both breasts. Additional support can be provided by a sternum support (15), which may or may not contain RF imaging coils. In this arrangement a total of 8 coil plates may be arranged to cover imaging of both breasts. Additionally, coils may be attached to any other coil in the system through a mechanical connection. This may introduce the coil into the array at a well defined position such that it provides improved decoupling between coils. The connection can be made at various left/right positions such that various electrical connections associated with unique mechanical positions such that unique decoupling and electrical connections can be made.

Figure 7C:
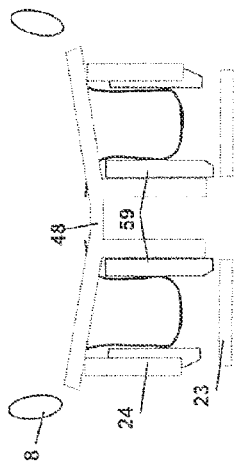

Coil plates may house transmit, receive or transceive coils, or any combination of these coils. In FIG. 7C, the two posterior coil plates (48), the sternum support (15), the two medial coil plates (47) are combined into one combined support and imaging structure. This medial support structure can be removed from the main support as would be necessary for interventions performed in the medial direction to ensure full breast access. The medial support structure may also be hollow, such that various W coils can be placed into position while that patient is still atop the structure.

Shown here medial compression plates do no house any medial coil plates. Instead all of the RF antennae are integrated into this medial support structure. This embodiment may have coils on each medial face, in the sternum face, and throughout the posterior structure. In this arrangement the coils can be decoupled from one another through traditional means as the coils do not move relative to one another. This can be extended to include any combination of coil plates and support structures.

An alternative arrangement of coils is demonstrated in FIG. 7D, E, F. Here the function of compression of the breast and the placement of the coils have been separated. An implementation for a unilateral coil geometry is demonstrated in FIG. 7D, the lateral coil (24) is attached through connecting members to the medial coil (47). These connecting members may i) house electrical connectors that complete circuits on the lateral or medial coil arrays such that they are activated for imaging, ii) may provide connections between lateral and medial coils for purposes of decoupling lateral and medial coils, iii) may house additional coils or segments of coils that can be used to contribute to the array of active coils.

Additionally, coils positioned in the posterior or anterior positions relative to the breast can be integrated at fixed positions relative to (24) and (47). In this way the coils are at known positions relative to each other, where decoupling strategies such as inductive or capacitive decoupling can be used to reduce the coupling interactions between all coil elements. Compression members can be attached to the members connecting the lateral and medial coils such that the breast may be compressed without moving the coils. In FIG. 7E, a bilateral implementation extends this concept to attach lateral coils (24) to a large medial coil which can house coil elements in the posterior and medial positions relative to the breast, where the compression plates can move relative to the coils to enable compression as required. In FIG. 7F, the posterior coil is integrated with the medial coils. In this arrangement all coils are at known positions to one another and therefore can be appropriately decoupled. No compression plates are presented in this implementation. The ability to numerous connect subsets of coils into a primary set of coils that is attached to the MRI is a novel and fundamental concept.

In all of these embodiments, the lateral, medial, anterior or posterior coils can be interchanged with other coils such that the coils can be arranged such that they can be sized as is appropriate to the geometry of the breast.

The proposed coil structures in FIG. 7 enable coils to be placed close to the breast, or to encase the breast with numerous coils for various imaging applications. Additionally, these coils can be removed or interchanged with coils that are appropriate sizes relative to the anatomy being imaged. A set of various coils may comprise a kit that enables imaging of various breast sizes, including:

One embodiment where there are coils for unilateral imaging and different coils for bilateral imaging. Additional embodiments include unilateral and lateral coils that may be provided in a set of coils of different sizes including the following options: In one embodiment there will be coils provided in one size for a medium sized breast. In another embodiment there will be two sized breast coils for medium and large sized breasts. In another embodiment there will be three sizes of breast coil for small medium and large sized breasts. Other embodiments include more than three sizes of breast. For surface coils housed in medial and lateral plates the size of the coil would be primarily changed in the Anterior/Posterior direction. As a non limiting example of appropriate segmentation of sizes, the range of sizes for these coils in the anterior/posterior direction would be (large coil-20-25 cm, medium coil 20-15 cm, small coil 15-7.5 cm). An appropriate coil dimension in the superior/inferior direction as a combined set, would be 15-25 cm and would not vary more than 50% of the total size according to small to large coil designation.

In another embodiment, one of these breast coils will be in a configuration that is optimal for mastectomy imaging. In this geometry the coils would be positioned in the plate parallel to the chest wall. The field of view of these coils would range from 20-35 cm, depending on patient size. The optimal arrangement is such that the depth of the field of view of these coils is small and does not penetrate deep into the chest wall region, such that the ratio of the field of view to the imaging depth of the coil may be better 5:1 to 20:1. Various coil arrangements may be used to cover this field of view, including a set of butterfly, loop and transmission line coils such combinations are presented in FIG. 6. Optimally loop coils in the array would consist of coils longer than wide (aspect at least 2:1) directed with the long axis in the direction of the main magnetic field, parallel to the chest wall. Butterfly coils would optimally be directed with the long axis directed from patient left to right, while transmission line, or strip-line coils would be directed with long axis along the main magnetic field.

These coil plates are provided as straight, or curved to match the chest. Patient may be supported by the primary structure of the bed such that the mastectomy region or surgical scar. Alternatively these plates could be made of a flex circuit such that the coils conform to the chest anatomy. The concept of using a kit of coils of different sizes is unique and not presented in the prior art. There has been no indication of the use of specialized coils used for mastectomy imaging.

This concept of modular coil plates that comprise an imaging array is demonstrated In FIG. 8. Here a set of coil plates can be arranged as either a set of four moveable plates (FIG. 8A, D, G, J) 2 movable plates with 1 fixed medial array (FIG. 8B, E, H, K) or one fixed medial array with two attachable lateral plates (FIG. 8C, F, I, L). In each of these geometries loop, butterfly (either with two or more lobes), saddle, transmission line or the like can be integrated. In FIG. 8A, both medial and lateral plate can move relative to each other. Demonstrated in FIG. 8A are two large lateral loop coils, with opposing medial butterfly coils. This combination ensures there is minimal decoupling between the lateral and medial coils. Additionally, the medial coils may be comprised of transmission line coils such that the ground planes on the facing sides of the medial coils ensure these coils do not couple, thus improving performance of the coil array. Alternatively butterfly coils may be used as lateral coils and loop coils as medial coils. Alternatively one butterfly coil can be used laterally, one medially on the opposing side, while loop coils can be used opposed to these butterfly coils. In this way all coils will be decoupled.

An alternative geometry is presented in FIG. 8B, where the medial coils are attached to the same structure and overlapped or decoupled using circuitry. In this configuration the medial coils cannot be moved relative to each other. In an alternative arrangement in FIG. 8C, the medial and lateral coils cannot be moved relative to each other, instead they are locked together in a fixed geometry. Represented in 8C is a planer geometry, whereas in FIG. 8F, 8I and 8L the lateral coil geometry is curved.

FIG. 8A, 8B, 8C all represent 4 coil geometries, whereas FIG. 8D, 8E, 8F are 6 coil geometries. The preferred geometry for FIGS. 8D and 8E are two lateral loop coils, decoupled from one another, with one large medial butterfly coil directed towards each loop coil on each side of the breast. The medial butterfly coil should extend and bend towards the chest wall with one lobe of the butterfly larger than the other. The lateral coil should be positioned more posterior relative to the medial coil so as to access the patients chest wall and axial. The use of a butterfly that has a non-symmetry lobe presentation and that bends towards the chest as presented is a novel invention and not presented in anyway in the prior art. This is essential for proper imaging of the sternum area.

In FIG. 8F, the medial coils are decoupled by overlapping, while the lateral coil has two large apertures to enable access to the breast. In this geometry the lateral coils attach to the medial coil at a number of connection points. These attachment points may be used to select, or activate coils in the medial array, where the coils are selected based on which coils are used laterally. Alternatively these connection points complete coil geometries by way of adding a conductor element to the medial or lateral coil arrays through the process of connection of the lateral and medial sections.

FIG. 8G, 8H, represent 8 coil geometries where three lateral coils are used and one medial butterfly coil per side. FIG. 8H shows a non-symmetric butterfly coil where the posterior portion of the loop is larger than the anterior (lower) part of the coil. In this way the lateral and medial coils are decoupled when the lateral coil is positioned more posterior than the butterfly coil. Variations of such a geometry includes decoupling the lateral coils from each other through i) overlap in excess of the required amount between the central and outer coils with corrective inductive or capacitive decoupling, ii) overlap the exact amount between the outer and central coils with no required inductive or capacitive decoupling, iii) overlap less than the required amount with corrective inductive or capacitive decoupling.

FIG. 8I shows two medial coils per side with numerous coils contained in the lateral coil attachment. In this arrangement several attachment points, serving as both structural and electrical connections, are presented in the superior and inferior locations each per side with an additional connection anterior to the arrangement. This way multiple electrical connections may be made between the lateral and medial arrays. Any number of connection points may be used without deviating from the spirit of detachable coils and should not be limiting.

FIG. 8J demonstrates two lateral and two medial coils. The lateral and medial coils are slightly overlapped for decoupling. Any combination of loop and vertically oriented butterfly coils are intrinsically decoupled in this geometry. In FIG. 8K eight medial coils are located per side with eight lateral coils. This geometry is easily expanded so as to include numerous, vertically oriented loop coils and butterfly coils. In this geometry each coil covers the breast in the Anterior/Posterior direction, while coils have limited field of view in the Superior/Inferior direction, which enables parallel imaging in the left/right and superior/inferior direction. These two parallel imaging directions are optimal for breast imaging in the prone orientation. FIG. 8L demonstrates a final geometry where the mechanical/electrical connection can be made from the anterior approach so as not to risk pinching the patient as the coil is connected.

Additional very high densities of coils can be used in the proposed coil arrangements. The addition of coils in the posterior region, with a large aperture for admitting the breast(s), and/or addition of coils in the anterior regions provide various alternative placements for coils within the presented coil configurations. In the ideal case, the magnetic flux lines associated with the coils arranged on these coil geometries would be orthogonal to the main magnetic field of the MRI ($B_0$), so as to maximize collection of the MRI signal.

As an example of a dense coil geometry that can be used with a 16 channel MRI system, a bilateral geometry could be presented where 8 butterfly coils may be located on the medial coil plates, or in the medial sternum support. Across from these butterfly coils could be 8 loop coils. This is repeated for both left and right breast volume. These coils would be longer in the anterior direction than in the superior direction, and decoupled pair-wise from each other on their respective coil plates. For a unilateral arrangement, 16 coils could be used per coil plate. In order to optimize imaging for parallel imaging, the geometries of the coils can be slightly modified so as to differentiate their coil sensitivity profiles. This is performed by modifying the butterfly trace by extending the width, height, or angle of the conductor traces.

This arrangement can be scaled up or down from anywhere from 1 coil per plate, to 16 coils per plate, while still maintaining sufficient penetration into the breast tissue over the clinically relevant field of view. This provides an arrangement where a very highly parallelized geometry can be used for breast imaging. Alternatively, transmission line coils can be used in either in a hybrid loop geometry as a replacement for the loop coils in the previous description, or transmission lines in a straight configuration, used in combination with the loop coils. These variations are presented in FIG. 6, however they are presented here in the context of the modular array system. Additionally, where loop and butterfly coils may be used as a quadrature pair, the signal to noise can be improved further through quadrature combination of those pairs to a single signal line.

It should also be noted that in all cases, curved or conformal coil plates may be utilized without departing from the spirit of the invention. Such plate arrangements may be useful when imaging other anatomies such as knees, elbows, wrists, ankles, etc. Interchanging these coil plates provides for all of the advantages discussed thus far for breast imaging, because it is hereby possible to support or immobilize the anatomy, advance to the scan position for imaging, return to the home position (outside of the magnet), and remove the coil plates either for access to the tissue or to replace them with an alternate set of coil plates and then re-image in order to optimize imaging and to provide the ability to deliver additional imaging and interventional devices without moving the anatomy from the configuration in which it was initially imaged.

Selection of a subset of coils to act as transmit coils and other coils to act as receive coils provides a significant benefit in imaging applications where SAR limitations need to be considered (Specific Absorption Rate refers to the rate of energy deposition in tissue due to RF pulses transmitted by the MRI. Transmitting with relatively small local coils reduces tissue heating compared with transmitting RF through the entire body). In one embodiment, the anterior and posterior coil arrays can be used as transmit coils, where the combined fields provide a substantially uniform transmit field, while the medial and lateral coils can be used as receive coils. The roles of the coils could also be the opposite, where the anterior and posterior coils receive and the medial and lateral transmit.

The imaging methods presented can be performed with any combination of plate geometries. These plates may be arranged in a manner that they can move relative to one another, or may be fixed relative to one another. In the preferable arrangement these coils would be positioned as close to the anatomy as possible, while attempting to minimize coupling between coils. Coupling can also be minimized by sizing the coils appropriately to the anatomy being imaged. By selecting and attaching coil elements whose sensitivity profile is just sufficiently large to image the desired volume, but which does not extend far enough to couple to other coil elements.

An alternate embodiment of a reconfigurable coil array comprises a circuit board having multiple layers of conductive traces, which traces are insulated from one another. These traces, along with their attendant capacitors, inductors and blocking circuitry constitute individual coils, such that a multiplicity of coils is present on a single plate. These coils may be loop, butterfly, opposed solenoid, or transmission line types. Means are provided in this embodiment for selection and signal connection of one or more of these coils at a time, while a number of other coils are disabled by being opened (electrically), detuned, blocked or short circuited. This coil selection means may comprise mechanical switching of conductive pathways or solid state electrical switching, either at the coil end or the MRI end of the signal coupling means.

Additionally, the act of mechanically affixing the coil plate to a fixation means such as a compression plate could activate and deactivate selected coil elements on the coil plate. The fixation means could effect this activation and deactivation using mechanical keys or electrical plugs that connect some coil elements and detune, terminate or block others.

The electrical connection means of each coil would interface with a receiving connector integrated with the mechanical fixation means. This pair of mating connectors could be shaped to accept connection one or more positions, so that the orientation in which the connectors meet determines which coil elements are active, and/or determines the polarity of each coil. For example, rotating the coil plate 180 degrees before plugging it in would reverse the polarity of the coil's output. Means would be present in the connector and blocking network to ensure that the blocking signal used with receive-only coils always arrived with the correct polarity. Rotating the coil plate 90 degrees (perhaps from a sagittal to a coronal plane, for example) before connecting it would have the effect of activating different coil elements within the coil plate which coil elements produce a sensitivity profile befitting the plate's orientation and relative position to the anatomy.

Interchanging these coil arrangements for different imaging applications in the breast or in other reconfigurable anatomy can be used to optimize SNR and field-of-view for:

i) Bilateral anatomy imaging—maximize number of coils and optimize their sensitivity profiles for bilateral volume.

ii) Unilateral anatomy imaging—maximize number of coils and optimize their sensitivity profiles in a single volume.

iii) Interventional procedures—maximize number of coils and optimize their sensitivity profiles while still providing for appropriate access of physician's hands, line-of sight, and interventional and imaging devices.

iv) Anatomy imaging in different conformations—maximize number of coils and optimize their sensitivity profiles in a reconfigured anatomical position.

Anatomical Positioning

Figure 9A:
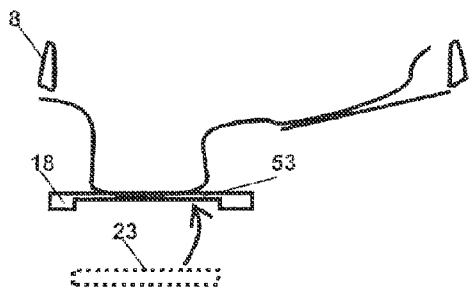
FIG. 9—Shows multiple views of breast compressed in the up/down or superior/inferior direction. A. Shows a breast compressed by a compression plate directed from the anterior direction towards the posterior. B. Shows a coil inserted in the compression plate. C. Shows compression of two breasts from the anterior direction. D. Shows a sagittal view of the anterior compression plate. E. Shows an oblique pivoting compression plate compressing the breast from the anterior direction. F. Shows a sagittal view of e.
Figure 9B:
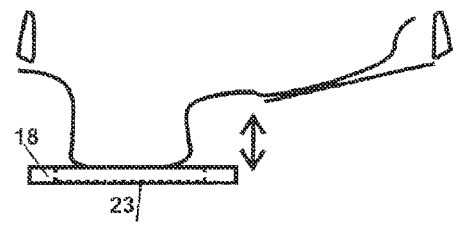
Figure 9C:
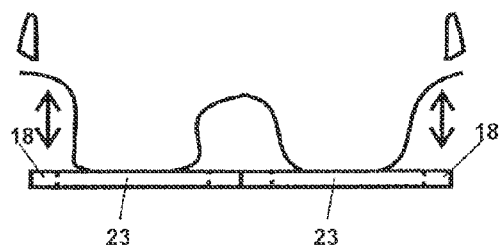
Figure 9D:
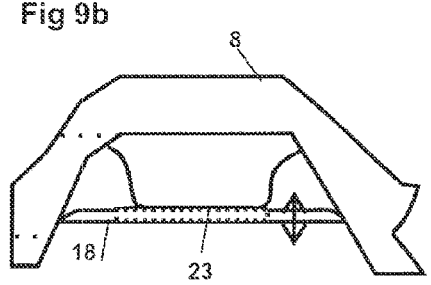
Figure 9E:
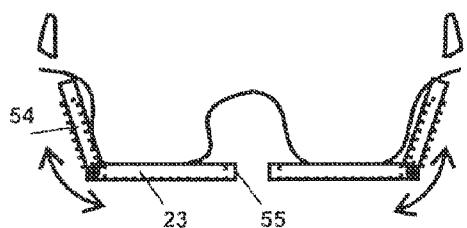
Figure 9F:
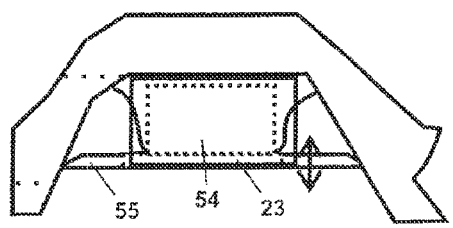

A patient can also be imaged with breasts in various geometries through compression provided from several directions. The concept can be extended to other anatomies that are reconfigured to suit a clinical or diagnostic need—i.e. it may be desirable to image in one anatomical configuration for optimal image quality, and in another to obtain images in a configuration representative of surgery, for example. As depicted in FIG. 9A. a breast may be compressed towards the chest wall using a compression plate (18) that can move in the anterior/posterior direction. The plate presented in this figure also provides an aperture which is covered by a compression membrane (53). Within this plate there may be a coil plate inserted as depicted in FIG. 9b. By moving this compression plate containing the coils close to the breast, good immobilization and high SNR can be obtained. By removing the coil plate (23) there may be access to the breast for other imaging modalities providing the membrane is substantially permeable to that modality. For instance if an acoustical membrane is used, an ultrasound transducer can be used to image the breast, while the four sides of the breast remain accessible for interventional purposes. This concept is shown in FIG. 9C in a bilateral imaging application in the axial view, and in the sagittal view in FIG. 9D. An alternate embodiment of the compression plate is shown in FIG. 9E, where the compression plate consists of a pivoting oblique member (55). In each of these compression members there are one or more or apertures in which coil plates can be fixed, and one or more membranes (which may have coils removeably fixed across them). This is demonstrated in the sagittal view in FIG. 9F. The benefit of this arrangement is that the breast is more completely immobilized and the immobilization system can support a greater number and variety of coils. The compression plates may also support a conformal plate such that the breast is more evenly compressed in the orientation.

Another benefit of the proposed system is the ability to support conformal plates or immobilization devices. As an extension of the position and orientation-adjustable compression plate, a conformal immobilization plate (56) or membrane (such as a thermally setting mesh) could be positioned on the breast while the patient is in the position used for surgery, such as the supine position as indicated in FIG. 10A. The patient's breast position could be maintained while the patient is rotated to another position, such as the prone position, and positioned on the main support structure of a dedicated stretcher-based coil, or a tabletop add-on coil. The open architecture of the system provides for the addition of such a conformal immobilization structure. A set of imaging coils may be added to these plates, either as a coil supported by an oblique compression plate (72) as shown in FIG. 10B, or as a conformal arrangement of coils supported on the conformal immobilization plate (56). This same arrangement is shown in FIG. 10c in a sagittal view where the oblique compression is capable of moving up/down and rotating. The ability to position the breast in two different conformations while the patient remains on the main support structure is important for MRI interventions and when imaging may be required for determination of pre-surgical breast cancer extent. The repositioning should be done such that a set of MR images may be obtained while positioned in a standard imaging orientation (i.e. uncompressed with the patient prone, or compressed in the mediamateral orientation with the patient prone), and a set of images that may be similar to the position during surgery (patient laying supine). This way the tumor position can be correlated between both positions, or in positions in-between the two end positions. These two imaging positions can also be utilized to ensure a localization wire, or other surgical marking device remains in position while in another geometry, or to provide for another position for minimally invasive treatment of cancers. This is demonstrated in FIG. 10D, where a compressed breast is demonstrated in an axial view compressed in a medial/lateral direction, and a localization wire (58) has been positioned through the lesion (57) of interest. In FIG. 10E, all coils and compression plates are removed and the breast can be freely manipulated with the patient on the apparatus.

An anterior conformal compression plate can then be introduced as presented in FIG. 10F to compress the breast into a conformation similar to that of breast surgery, and to deliver a coil plate into proximity with the breast for imaging. In this way the breast can be compressed in a preferred orientation for a particular clinical application, and RF coils can be positioned as close to the breast as possible to ensure high SNR images can be acquired.

The invention is specifically presented in the figures for breast imaging applications, however it may be applied to any anatomy in which bilateral imaging or unilateral imaging may be preferred, or any situation where the patient support and immobilization is performed independently of the coil system.

Dedicated Body Imaging Applications

Another example where the presented methods and apparatus can be applied includes body imaging applications. In this application a dedicated body imaging stretcher (61) with a large interventional volume provides an access point in which modular support structures and coil arrangements can be positioned, affixed and removed. Applications for this system include cardiac, lung, musculo-skeletal, spine, liver and kidney imaging, as well as interventions for these anatomies. In FIG. 11A, the patient (4) is supported by an MRI body support structure (60) where anterior (62) and posterior plates (63) are used to position coils close to the patient. In an analogous manner to the breast imaging application, various coil arrays can be introduced by way of coil plates. Demonstrated in FIG. 11B is a large field of view coil array (64) and a small field of view coil array (65), typically used for higher SNR imaging applications. The coil plates are inserted into the support plates as demonstrated in FIG. 11C. In FIG. 11D, the small field of view coil array is put in place of the large coil array, and positioned appropriately over the target anatomy, so as to image with high signal to noise in a region of interest.

Additionally, coils tuned to different frequencies, optimized for a particular imaging or intervention application may be easily interchanged while the patient is maintained in the same conformation. For instance, for lung imaging a coil array may be required for contrast-enhanced imaging of blood flow as well as imaging hyper-polarized gas or the like for imaging of ventilation. For cardiac applications, a coil may be provided to excite or image a particular species associated with a novel intravascular contrast agent. Each of the coils can be appropriately tuned to detect, or to excite a particular species of interest. Additional lateral or oblique plates may be integrated into the apparatus as required. These plates may provide lateral support for a patient, provide attachment points for probes and devices, and may provide additional attachment points for coil systems for improved imaging. Additionally, the support plates may provide access apertures and/or guidance means for intervention, or imaging with other modalities (X-ray, Ultrasound, Optical, Infrared, etc). The dedicated stretcher/special-purpose tabletop system and modular arrangement of subcomponents provides all of the advantages realized in the breast application.

An alternate embodiment of the present invention expands on the same concept for prostate, gynecological and colon imaging and intervention. In a further implementation this sheath concept can be used for intravascular imaging or intraoperative imaging and the like. As presented in FIG. 12, a dedicated prostate stretcher and tabletop system provides additional access to enable modular coil and patient support apparatus to be reconfigured for various stages of the same imaging/intervention procedure, for procedures with different patients, or for different types of procedures. The major differential feature as presented is the addition of a support apparatus that can be inserted inside of the patient. The support apparatus, not shown in this figure may consist of an articulating arm or support which holds a sheath or introducer into the body. By maintaining this sheath in a fixed position, various coils and devices can be inserted while remaining in a fixed relative position to the patient and other devices. This is demonstrated in FIG. 12A where an anterior coil support (62) (FIG. 12C), a posterior coil support (63) ( FIG. 12E) and an internal coil sheath (68) (FIG. 12D) all support a variety of coil arrangements. Various coil plates can be introduced to these support/immobilization structures depending on the application. The anterior plate (62) holds the patient's hips in a fixed position, as shown in FIG. 12B, while providing a means of attachment for the coil array. This may be effected by a support arm which maintains the position of the anterior coil and prostate sheath so that they are held at a fixed position relative to the patient. The prostate sheath may be permeable to various imaging modalities such as ultrasound and may provide interventional access ports to facilitate intervention of the prostate.

The sheath (68) may also be made from a flexible membrane which can be expanded. In this way, a probe can be inserted into the sheath and be inflated or mechanically enlarged so as to immobilize the surrounding anatomy. In the specific application of prostate imaging, the solid plastic walls of the probe should be expanded so as to press against the rectal wall. In this way the coils can be positioned in very close contact to the prostate so as to maximize signal acquisition. Additionally, if the plastic is made from a material with susceptibility close to that of the tissue, then there will be no deleterious image artifacts that may affect imaging of the prostate area. Additionally, a vent or aperture should be provided in the center of the coil, or on the outer regions of the coil such that gases can be vented during the procedure to improve patient comfort and limit peristaltic motion.

According to the invention, numerous techniques, procedures and methods make good use of the various embodiments of the invention, as illustrated by the following specific examples:

Bilateral imaging with all available channels utilized
Unilateral imaging with all available channels utilized
Interventional imaging with coils selected to provide open access Breast imaging (bilateral or unilateral) with the breast uncompressed, compressed medial/lateral to immobilize for better imaging, compressed against the chest wall, or with oblique compression. (Compression is performed to improve imaging (i.e. less motion), reduce motion during intervention, position the breast to match surgical position, or to match other imaging positions (US, X-ray, CT)).

Imaging where coils may be exchanged for coils that are tuned for other desired frequencies—i.e. higher field (3.0T), spectroscopy (Na, $C_{13}$, F, etc), or to match species associated with novel contrast agents. In the example of lung cancer imaging, coils can be tuned to hydrogen for contrast enhanced studies, and exchanged for coil tuned to hyper-polarized gases to image the ventilation cycle.

Imaging where coils are exchanged for coils better sized to match the anatomy, for example sizing coils to suit the size of a breast.

Imaging where coils are exchanged for coils with higher acceleration factors in preferred imaging applications.

Imaging where coils are exchanged for new coil designs, or designs that take advantage of the greater number of data channels available on the MRI, while keeping the same patient support, or dedicated stretcher design.

Imaging where non-functional coils can be removed and exchanged for functioning coils instead of replacing the entire system, or in the case of cryogen cooled coils, exchanging the coils for coils that are refilled with cryogen, in the case of wireless coils—recharging the batteries, in the case of sterilizable coils—cleaning.

Imaging and intervention for body applications using a dedicated body imaging stretcher and tabletop.

Imaging and intervention for prostate applications using a dedicated prostate stretcher and tabletop.

The foregoing description of the invention is not intended to describe every object, feature, advantage, and implementation of the present invention. While the description of the embodiments of the invention is focused on applications for breast imaging, it will be understood by those skilled in the art that the present invention has utility to applications elsewhere in the body. The primary difference would relate to the geometry of the coils and their relative positioning. The fundamental concept of separation of patient support, anatomy immobilization and RF systems has wide ranging benefits.

All patents and printed publications referenced herein are hereby incorporated by reference into the specification hereof, each in its respective entirety.

A number of techniques, methodologies, apparatus and systems have been proposed to improve the imaging of tissue using MRI. Including, but not limited to:

Novel architecture for RF imaging systems including:
　Coils independent from the support structure
　Coils that are interchangeable
　Coils that can be positioned in varying positions close to the patient anatomy.
　Coils embedded in secondary structures such as repositionable compression plates
Techniques and mechanisms for interchanging coil systems separable from the patient support apparatus.
Novel compression mechanisms appropriate for anatomical compression in various orientations and configurations.
Interchangeable compression systems.
Compression systems with apertures to enable
　Coil insertion and fixation.
　Membranes permeable to various imaging modalities
　Interventional and imaging device access
Interchangeable coil systems with various options for coil signal transmission including—cables, inductive coupling, optical transmission, telemetric transmission.
Interchangeable coils which integrate analog-to-digital conversion capability so that cable-based or telemetric connection may convey digital rather than analog information.
Novel coil arrangements for densely packed coil arrays including combinations of loop, butterfly, saddle, opposed solenoid and transmission line coils.
Secondary support structures providing optimal patient positioning, support and immobilization options.
Secondary support structures with integrated RF coils or with means of affixing RF coils.
Cable routing to ensure cables do not contact the patient.
Coil recharging using an external charging module when coils require battery power
Coils that use received RF energy to charge an energy storage device.
Coil cryogen filling using an external charging module when coils are cryogen cooled
Benefits of such a system are:
better SNR due to more coils and more appropriately sized coils closer to the patient anatomy.
different coil systems for parallel imaging applications, giving the user flexibility for either imaging for intervention or for diagnostic imaging applications.
flexible imaging such that various imaging techniques can be performed with the patient in the same conformation but with coils specialized for different imaging, i.e. 1.5T, 3.0T, Na, K, $C_{13}$ imaging.
reduced downtime as a single defective coil does not necessitate replacement of the entire coil system—only a single coil plate or coil element need be replaced.
upgradeable system to the user such that subsequent coil requirements or an MRI upgrade would only require a subsystem of the coil system to be purchased, as opposed to an entirely new coil system with attendant housing/patient support structure.
ability to image the breast in various compression shapes with minor modification to the structure while the patient is maintained in the same position on the apparatus. Time is critical in this application as imaging should be performed while the injected MRI contrast agent is still providing imaging contrast. This leads to the ability to show a contrast enhanced lesion in various compression conditions with a single contrast agent injection. Various compression states include:

uncompressed
compressed medial-lateral
compressed anterior/posterior
oblique compression
conformal immobilization and compression of the breast
ability to physically remove, substitute and replace the compression system and the coil system while the patient is maintained on the apparatus. This allows improved access to the imaged anatomy for additional imaging, interventions and treatment. This is possible when there is a significant aperture provided as in a dedicated stretcher-based dedicated tabletop The technology of the present invention includes a patient support structure for a patient comprising a connected or continuous area that support at least the head, chest, abdomen and legs of a patient, the support structure having at least one component support structure that receives and releases at least one RF coil system adjacent the patient, the at least one component support structure allowing positioning of the at least one RF coil system adjacent one or more of the head, chest, abdomen and legs of the patient. The patient support structure may have at least one specific component support structure for coils for at least one location on the patient support structure that accommodates at least one of female breasts, female genitalia or male genitalia. There may be at least one specific component support structure for coils for at least one location on the patient support structure that accommodates at least one of female or male breasts, female genitalia, prostate and colon, and torso of a patient. There may be at least one location of the component support structure has the component support structure has a glide support for enabling insertion of different coil structures on supports with common glide engaging features. The patient support structure may have at least one location of the component support structure with a glide support for enabling insertion of different coil structures on supports with common glide engaging features. The patient support structure may have coil structures with an engaging element that connects to a communication port, material flow port or power port on the patient support structure. The patient support structure may comprise a stretcher on wheels, and the stretcher may have engaging elements for engaging the RF coil system of the stretcher to the RF system on a magnetic resonance imager. The patient support structure may have a specific location accommodating positioning of female breast therein, the location is adjustable to accommodate breast of different sizes, and an RF coil system for assisting in the MR imaging of breast positioned in the location may be removed and replaced while breasts are positioned in the location without moving the compression system while in contact with the surface of the breasts. The patient support structure may have coils of different functionality selected from the group consisting of receiver antennae, transmitter antennae and transceiver antennae may be interchanged or placed in combinations of said antennae adjacent the location. The patient support structure may have at least one location with distributed thereabout a combination of transmission line coils, with the longest dimension in an anterior or posterior direction, disposed with loop and butterfly coils as alternating patterns on a) opposing plates, b) opposing structures, or c) co-planar on a plate. The patient support structure may have the at least one set of RF coils with at least two or at least four moveable lateral and medial coil plates containing intrinsically decoupled coils. The patient support structure may have the intrinsically decoupled coils selected from the group consisting of a) vertically oriented butterfly and loop coils, b) various transmission line coils with loops, c) transmission line coils and butterfly coils, d) multiple lobed butterfly coils in combination with a loop or transmission line coil, or the intrinsically decoupled coils are selected from the group consisting of a) horizontally oriented butterfly and loop coils, b) various transmission line coils with loops, c) transmission line coils and butterfly coils, d) multiple lobed butterfly coils in combination with a loop or transmission line coil. The patient support structure may have the RF coils enabled for signal transfer from the RF coils through attachment of the RF coils of the patient support structure to cables in an MR imager through at least one of:

1) Direct electrical connection
2) Brushes or sliding mechanical/electrical connectors;
3) Magnetically inductive connections; and
4) Signal transmissions.

The technology of this invention includes a method of performing an MRI imaging process on an individual subject comprising supporting the subject on the patient support structure of claim 1, adjusting the location to accommodate dimensions of the individual subject, positioning at least one set of RF coils adjacent the adjusted location, moving the support into the bore of an MR imager, and providing MR image data on the individual subject that is at least enhanced by data derived from the at least one set of RF coils. In the method, while or after the support has been moved into the bore of the MR imager, the at least one set of RF coils is engaged to an RF system in the MR imager. The RF system of the stretcher automatically communicatingly connects to the RF system of the magnetic resonance imager. In the method, an additional step is performed that is selected from the group consisting of automatically tuning of coils in the stretcher, preamplifiers in the patient support structure enhance signal reception, electrical shimming coils, sending RF signals by wireless signal transmission to a receiver external to the magnetic resonance imager and cryogenically cooling the coils in the patient support structure during MR imaging. The patient support structure may have at least one set of receiver antennae, transmit antennae and transceiver antennae which are exchanged at the at least one location.

This technology details specific coil arrangements, means of connecting these coils and utilization of these coils for specific imaging purposes. Additionally, the concept of interchangeable coils has been extended and includes the use of a charging station for electrical power, and for cryogen cooled coils, the use of cryogen filling stations. Additionally, the present system enables the ability to embed electronics into the patient support and stretcher electronics to facilitate advanced imaging application such as: automatic coil tuning of coils, pre-amplifiers for signal reception, electrical shimming coils, wireless signal transmission devices and cryogen cooling systems for the coils.

The RF antenna set includes interchangeable coils where the coils are coils tuned for different imaging species for a particular field strength and coils tuned for different field strength. Furthermore the RF antenna set may include interchangeable coils where the coils are sized to the patient anatomy including coils for:

Small breast size
Medium breast size
Large breast size
Chest wall

Among the types of RF antennae that may be used are a set of some of loop antennae, transmission line antennae and/or butterfly antennae. The coil configurations presented and combinations of configurations are unique. The use of arrays of coils on separate plates that are intrinsically decoupled from one another through the use of butterfly coils facing loop coils, or loop and transmission line coils is novel. The combination of vertically (longest dimension in the anterior/posterior direction) disposed loop and butterfly coils either in alternating patterns on opposing plates, on opposing structures, or co-planar on a plate, are also novel combinations of coil geometries. This geometry is intrinsically decoupled. The term "decoupled" or "inherently decoupled" "or intrinsically decoupled" is well understood in the Rf coil art. It is a term accepted to mean that the magnetic fields resulting from stimulation of the coils are not significantly in interference with each other. In terms of geometry, it would be that the fields are not 180 degrees in opposition, and that the field strength of each field is at least about 50%, preferably at least about 70%, more preferably at least about 85%, and most preferably at least 90% or 95% of the strength of a single field in the absence of any other fields. The combination of transmission line coils (longest dimension in the anterior/posterior direction) disposed loop and butterfly coils either in alternating patterns on opposing plates, on opposing structures, or co-planar on a plate, are also novel combinations of coil geometries. This geometry is intrinsically decoupled. The combination of butterfly coils and/or loop coils positioned in such a way that the top of the butterfly and/or loop coil is curved towards the chest wall is a novel structure.

The combination of asymmetric butterfly coils (longest dimension in the anterior/posterior direction, with larger lobe disposed in the posterior direction) positioned in such a way that a crosswise loop or similarly intrinsically decoupled coil geometry would be decoupled from the butterfly when positioned at a location more posterior than the butterfly coil central axis in the A/P direction.

The combination of butterfly coils in a fixed medial support structure such that the left and right sets of coils are substantially decoupled through the use of overlap, capacitive or inductive decoupling is also a novel structure. The combination of any of the above coil geometries with the use of volume coils is also a novel structure.

The combination of these decoupled coil geometries as receive coils, transmit coils or transceive coils is a novel structure. The configurations of these coils for bilateral imaging comes from the preferred set of:
1) moveable lateral and medial coil plates containing intrinsically decoupled coils (vertically oriented butterfly and loop coils), (various transmission line coils with loops), (transmission line coils and butterfly coils). (multiple lobed butterfly coils and any loop or transmission line coil).
2) movable lateral coil plates with a stationary sternum support with coils substantially oriented in the medial left and medial right directions that are decoupled from one another using decoupling circuitry.
3) Stationary sternum support with attached lateral coils in fixed positions. All coils are decoupled relative to each other using decoupling circuitry.
4) Arrangements in 1), 2) or 3) with an anterior coil and/or
5) Arrangements in 1), 2) or 3) with a posterior coil with an aperture The combination for the preferred sets may also be selected from the set of the following for sets of these coils for bilateral imaging from the set of:
6) 2 moveable lateral and medial coil plates containing intrinsically decoupled coils (vertically oriented butterfly and loop coils), (various transmission line coils with loops), (transmission line coils and butterfly coils). (multiple lobed butterfly coils and any loop or transmission line coil).
7) movable lateral coil plate with a stationary sternum support with coils substantially oriented in the medial left or medial right.
8) Stationary sternum support with attached lateral coil in fixed positions. All coils are decoupled relative to each other using decoupling circuitry.
9) Arrangements in 1), 2) or 3) with an anterior coil and/or
10) Arrangements in 1), 2) or 3) with a posterior coil with an aperture In the configurations where a fixed lateral coil is attached to a fixed sternum coil in a replaceable manner is a novel concept. This enables 1) completion coil circuits in the lateral or medial coils in order to activate the coils, 2) connection of the coils to appropriate coil decoupling circuitry so as to minimize coupling of all of the coils in an array, 3) Addition of coils to the coil array.

A preferred embodiment of the invention has been described in considerable detail. Many modifications and variations to the preferred embodiment described will be apparent to a person of ordinary skill in the art. Therefore, the invention should not be limited to the embodiment described.

The invention claimed is:

1. A patient support and magnetic resonance imaging (MRI) system for a patient, comprising:
a main support structure configured to support an anatomy of a patient;
a first component support structure moveably connected to the main support structure, wherein the first component support structure is configured to position a patient's tissue in a position for imaging; and
a first RF coil system configured to be received and releasably attached to the first component support structure so that first RF coil system is positioned adjacent to the patient's tissue, and is active when the first component support structure is locked in a position for imaging the patient's tissue;
wherein the first component support structure is configured to receive and release the first RF coil system.

2. The system of claim 1, wherein the first component support structure is configured to position the first RF coil system adjacent to the patient's tissue.

3. The system of claim 2, wherein the first component support structure is configured to provide a plurality of compression configurations for the patient's tissue.

4. The system of claim 1, wherein the first component support structure comprises at least one locking component to lock the first component support structure in position.

5. The system of claim 1, wherein the first component support structure is configured to move along an anterior-posterior plane.

6. The system of claim 1, wherein the first component support structure is configured to move along a medial-lateral plane.

7. The system of claim 6, wherein the main support structure comprises at least one track constructed and arranged along the medial-lateral plane, and wherein the first component support structure is moveably coupled to the track.

8. The system of claim 1, wherein the first RF coil system comprises a medial RF coil held by the first component support structure.

9. The system of claim 1, wherein the first RF coil systems comprises a lateral RF coil held by the first component support structure.

10. The system of claim 9, wherein the first component support structure is configured to provide unilateral imaging of one of a patient's breasts.

11. The system of claim 1, further comprising a second component support structure configured to receive a second RF coil, wherein the first RF coil is a lateral coil and the second RF coil is a medial coil held by respective first and second component support structures.

12. The system of claim 11, wherein the second component support structure is configured to lock in a position adjacent to the patient's tissue for imaging.

13. The system of claim 11, wherein the respective first and second component support structures are configured to be positioned for bilateral imaging of the tissue.

14. The system of claim 1, wherein the first component support structure is configured to receive and release at least one of an interventional and a guidance device.

15. The system of claim 14, wherein the interventional device is configured to provide at least one access aperture for interventional procedures on patient's tissue.

16. A method for magnetic resonance imaging (MRI) a patient, the method comprising:
    accepting a patient's tissue to be imaged into a main support structure;
    holding a first RF coil system with a first component support structure moveably attached to the main support structure, the first RF coil system being received and releasably attached to the first component support structure;
    moving the first component support structure and the first RF coil system relative to the main support structure into a position adjacent to the patient's tissue to be imaged thereby defining a first imaging configuration; and
    activating the first RF coil system and imaging, with an MRI imager, the patient's tissue with the first component support structure and the first RF coil system when in the first imaging configuration.

17. The method according to claim 16, further comprising locking the first component support structure and the first RF coil system into the first imaging configuration for imaging.

18. The method according to claim 16, further comprising providing a second component support structure housing a second RF coil system to define a second imaging configuration.

19. The method according to claim 18, further comprising moving at least one of the first and second component support structures having a respective RF coil system to define the second imaging configuration.

20. The method according to claim 19, further comprising imaging the patient's tissue according to the second imaging configuration.

* * * * *